United States Patent
Woodbine et al.

(10) Patent No.: US 12,420,020 B2
(45) Date of Patent: Sep. 23, 2025

(54) SYSTEM AND METHOD FOR MULTI-MODAL DOSING DEVICE

(71) Applicant: GoFire, Inc., Denver, CO (US)

(72) Inventors: John Jesse Woodbine, Lafayette, CO (US); Joseph Francis Keenan, Superior, CO (US); Peter William Calfee, Dorset, VT (US)

( * ) Notice: Subject to any disclaimer, the term of this patent is extended or adjusted under 35 U.S.C. 154(b) by 740 days.

(21) Appl. No.: 17/111,997

(22) Filed: Dec. 4, 2020

(65) Prior Publication Data
US 2021/0085887 A1    Mar. 25, 2021

Related U.S. Application Data

(63) Continuation of application No. 16/726,193, filed on Dec. 23, 2019, now Pat. No. 10,888,665.
(Continued)

(51) Int. Cl.
*A61M 11/04* (2006.01)
*A61J 7/00* (2006.01)
(Continued)

(52) U.S. Cl.
CPC ........ *A61M 5/31546* (2013.01); *A61J 7/0076* (2013.01); *A61M 5/1412* (2013.01);
(Continued)

(58) Field of Classification Search
CPC .......... A61J 7/0076; A61J 1/03; A61J 7/0084; A61M 35/003; A61M 2205/60; A61M 15/0081; A61M 2205/276
See application file for complete search history.

(56) References Cited

U.S. PATENT DOCUMENTS

| 4,934,358 A | 6/1990 | Nilsson et al. |
| 4,947,875 A | 8/1990 | Brooks et al. |

(Continued)

FOREIGN PATENT DOCUMENTS

| EP | 2399636 | 12/2011 |
| EP | 2207528 | 10/2013 |

(Continued)

OTHER PUBLICATIONS

Storz & Bickel GMBH & CO. KG. Crafty Remote Control, 20165, p. 1.

*Primary Examiner* — Margaret M Luarca
(74) *Attorney, Agent, or Firm* — Daniel W. Roberts; Law Offices of Daniel W. Roberts, LLC

(57) ABSTRACT

Provided is a system and method for multi-modal dosing of a product. The system provides a control base for coupling to one of a plurality of different cartridges containing product, at least two cartridges having different modalities of delivery—the coupled control base and selected cartridge providing a dosing device. Each cartridge has at least a unique identifier, which may be read by the control base and correlated through a database to confirm that the user is authorized to use the cartridge, and use of the cartridge for a dose of product will not conflict with other products received by the user and known to the system. Cartridges that are not coupled to the control base are non-functional and cannot dispense product as intended with the system. An associated method of use is also provided.

32 Claims, 12 Drawing Sheets

Related U.S. Application Data

(60) Provisional application No. 62/787,650, filed on Jan. 2, 2019.

(51) Int. Cl.
    *A61M 5/14* (2006.01)
    *A61M 5/24* (2006.01)
    *A61M 5/315* (2006.01)
    *A61M 35/00* (2006.01)

(52) U.S. Cl.
    CPC ............ *A61M 5/24* (2013.01); *A61M 11/041* (2013.01); *A61M 35/003* (2013.01); *A61M 2205/3327* (2013.01); *A61M 2205/3553* (2013.01); *A61M 2205/3584* (2013.01); *A61M 2205/50* (2013.01); *A61M 2205/60* (2013.01)

(56) References Cited

U.S. PATENT DOCUMENTS

| | | | |
|---|---|---|---|
| 5,284,133 A | 2/1994 | Burns et al. | |
| 6,772,756 B2 | 8/2004 | Shayan | |
| 6,814,083 B2 | 11/2004 | Likness et al. | |
| 6,830,046 B2 | 12/2004 | Blakley | |
| 7,088,914 B2 | 8/2006 | Whittle et al. | |
| 7,164,993 B2 | 1/2007 | Likness et al. | |
| 7,540,286 B2 | 6/2009 | Cross et al. | |
| 7,905,230 B2 | 3/2011 | Schuler | |
| 8,464,706 B2 | 6/2013 | Crockford et al. | |
| 8,550,069 B2 | 10/2013 | Alelov | |
| 8,602,037 B2 | 12/2013 | Inagaki | |
| 8,807,131 B1 * | 8/2014 | Tunnell | A61M 15/0021 128/200.14 |
| 8,851,068 B2 | 10/2014 | Cohen et al. | |
| 8,897,628 B2 | 11/2014 | Conley et al. | |
| 8,899,239 B2 | 12/2014 | Hon | |
| 8,910,630 B2 | 12/2014 | Todd | |
| 9,220,294 B2 | 12/2015 | McCullough | |
| 9,320,301 B2 | 4/2016 | Memari et al. | |
| 9,380,813 B2 | 7/2016 | McCullough | |
| 9,462,832 B2 | 10/2016 | Lord | |
| 2004/0069798 A1 * | 4/2004 | Grey | A61M 15/0083 222/52 |
| 2005/0277912 A1 | 12/2005 | John | |
| 2006/0092071 A1 | 5/2006 | Andermo | |
| 2006/0289005 A1 | 12/2006 | Jones | |
| 2010/0250280 A1 | 9/2010 | Sutherland | |
| 2011/0118694 A1 | 5/2011 | Yodfat | |
| 2012/0029442 A1 | 2/2012 | Boyd | |
| 2013/0220315 A1 | 8/2013 | Conley | |
| 2013/0245545 A1 | 9/2013 | Arnold | |
| 2013/0245604 A1 | 9/2013 | Kouyoumjian | |
| 2013/0340775 A1 | 12/2013 | Juster | |
| 2014/0000638 A1 | 1/2014 | Sebastian | |
| 2014/0116455 A1 | 5/2014 | Youn | |
| 2014/0202477 A1 | 7/2014 | Qi et al. | |
| 2014/0243749 A1 | 8/2014 | Edwards et al. | |
| 2014/0278250 A1 | 9/2014 | Smith et al. | |
| 2014/0322782 A1 | 10/2014 | Baym | |
| 2014/0345633 A1 | 11/2014 | Talon et al. | |
| 2014/0345635 A1 | 11/2014 | Rabinowitz et al. | |
| 2015/0039591 A1 | 2/2015 | Ding et al. | |
| 2015/0053217 A1 | 2/2015 | Steingraber et al. | |
| 2015/0136158 A1 | 5/2015 | Stevens et al. | |
| 2015/0142387 A1 | 5/2015 | Alarcon et al. | |
| 2015/0181945 A1 | 7/2015 | Tremblay | |
| 2015/0245660 A1 | 9/2015 | Lord | |
| 2015/0272220 A1 | 10/2015 | Spinka et al. | |
| 2015/0297859 A1 | 10/2015 | Spandorfer | |
| 2015/0320948 A1 | 11/2015 | Eicher | |
| 2015/0327596 A1 | 11/2015 | Alarcon et al. | |
| 2015/0332379 A1 | 11/2015 | Alarcon | |
| 2015/0366266 A1 | 12/2015 | Shabat | |
| 2016/0007651 A1 | 1/2016 | Ampolini et al. | |
| 2016/0021930 A1 | 1/2016 | Minskoff et al. | |
| 2016/0089508 A1 | 3/2016 | Smith et al. | |
| 2016/0106935 A1 | 4/2016 | Sezan | |
| 2016/0106936 A1 | 4/2016 | Kimmel | |
| 2016/0143361 A1 | 5/2016 | Juster et al. | |
| 2016/0157524 A1 | 6/2016 | Bowen et al. | |
| 2016/0200463 A1 | 7/2016 | Hodges | |
| 2016/0211693 A1 | 7/2016 | Stevens et al. | |
| 2016/0219932 A1 | 8/2016 | Glaser | |
| 2016/0219933 A1 | 8/2016 | Henry, Jr. et al. | |
| 2016/0219938 A1 | 8/2016 | Mamoun et al. | |
| 2016/0278435 A1 | 9/2016 | Choukroun et al. | |
| 2016/0309784 A1 | 10/2016 | Silvestrini et al. | |
| 2016/0309789 A1 | 10/2016 | Thomas, Jr. | |
| 2016/0325058 A1 | 11/2016 | Samson | |
| 2016/0331027 A1 | 11/2016 | Cameron | |
| 2016/0331913 A1 | 11/2016 | Bourque | |
| 2016/0337141 A1 | 11/2016 | Cameron | |
| 2016/0356751 A1 | 12/2016 | Blackley | |
| 2016/0363570 A1 | 12/2016 | Blackley | |
| 2016/0363917 A1 | 12/2016 | Blackley | |
| 2017/0014582 A1 | 1/2017 | Skoda | |
| 2018/0043114 A1 | 2/2018 | Shears | |
| 2018/0177958 A1 | 6/2018 | Wilder et al. | |
| 2018/0263283 A1 | 9/2018 | Popplewell | |
| 2018/0263288 A1 | 9/2018 | Goldstein | |
| 2018/0353682 A1 | 12/2018 | Laurence | |
| 2019/0111220 A1 | 4/2019 | Richardson | |
| 2019/0240430 A1 * | 8/2019 | Jackson | A61M 15/0065 |
| 2019/0325287 A1 | 10/2019 | Strange | |

FOREIGN PATENT DOCUMENTS

| | | |
|---|---|---|
| EP | 3099363 | 12/2016 |
| EP | 3102266 | 12/2016 |
| GB | 2524779 | 10/2015 |
| KR | 2015065072 | 6/2015 |
| WO | WO03097141 | 11/2003 |
| WO | WO2016009202 | 1/2016 |
| WO | WO2016050247 | 4/2016 |
| WO | WO2016064906 | 4/2016 |
| WO | WO2016172802 | 11/2016 |
| WO | WO2016187695 | 12/2016 |

* cited by examiner

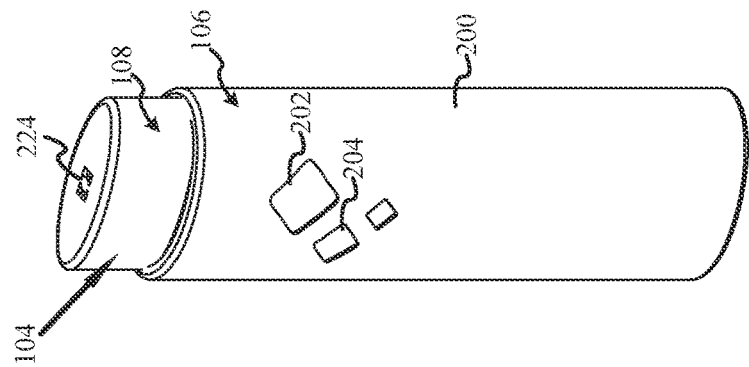
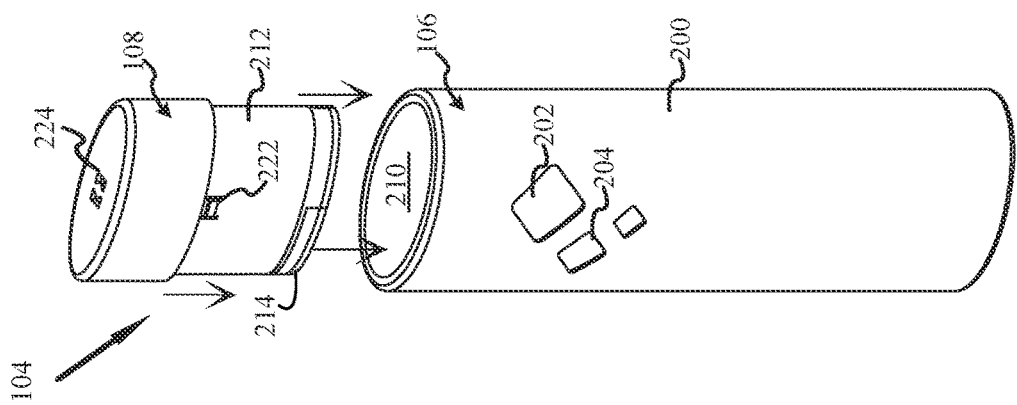
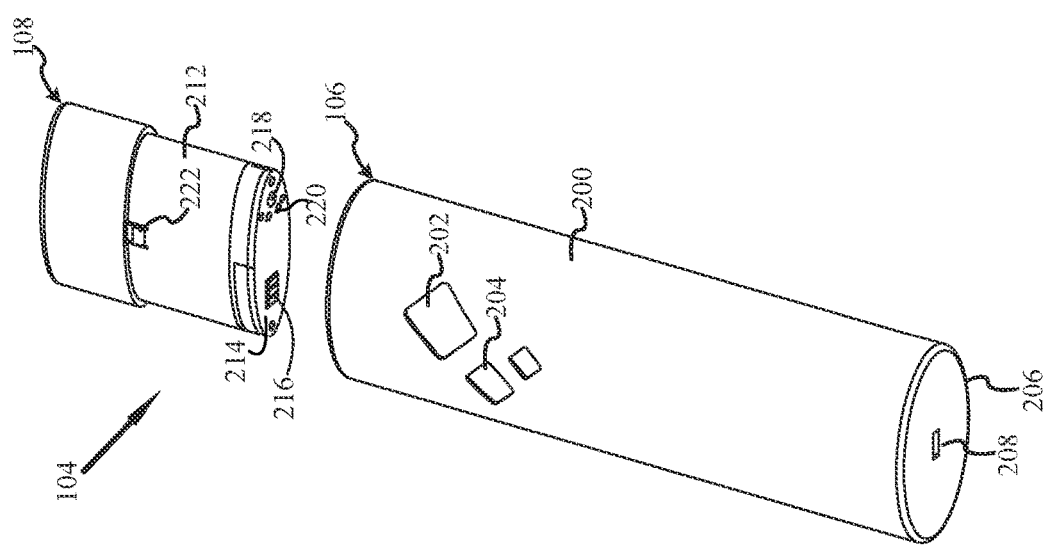

FIG. 2D
FIG. 2E
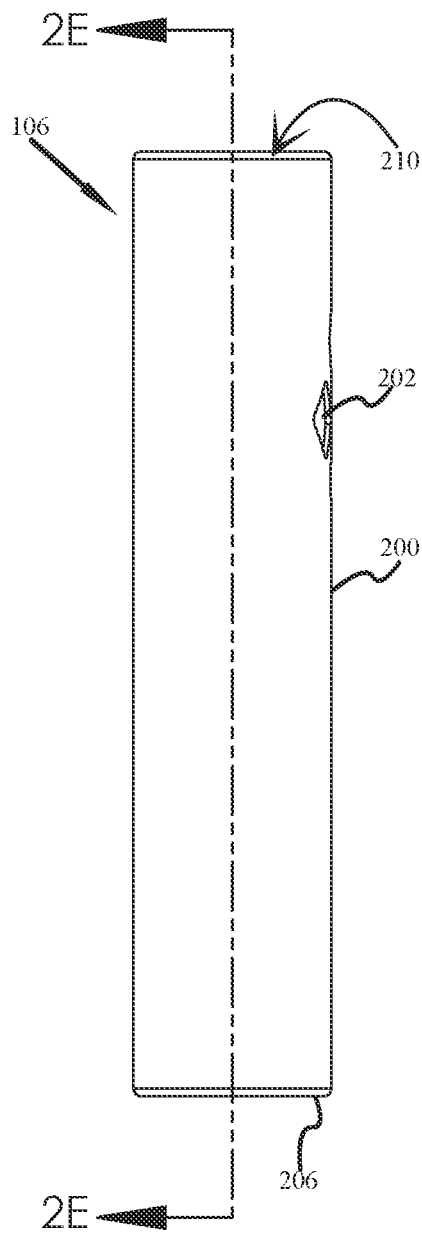
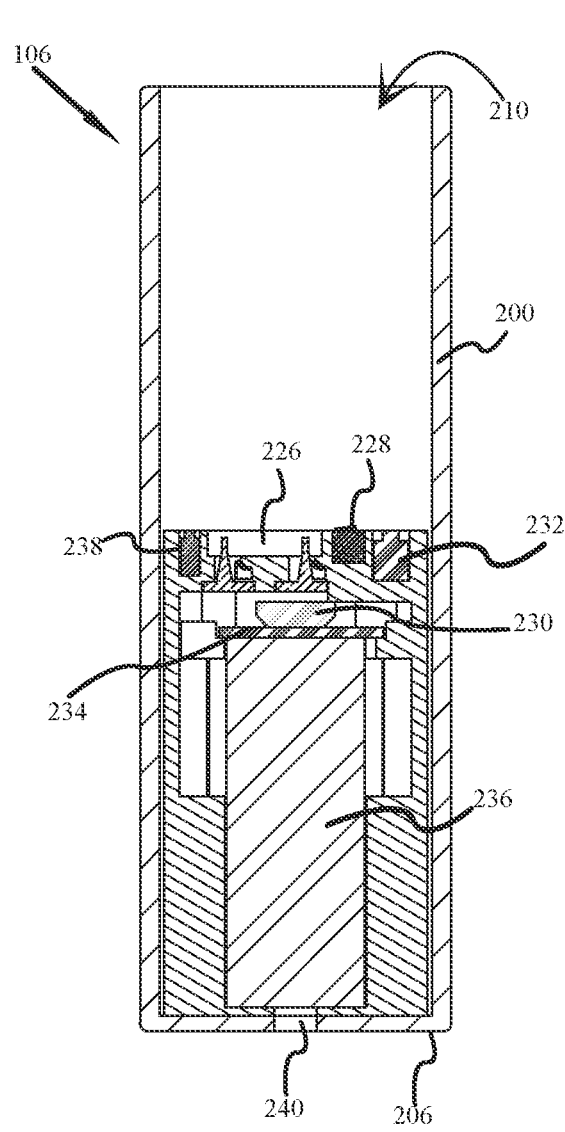

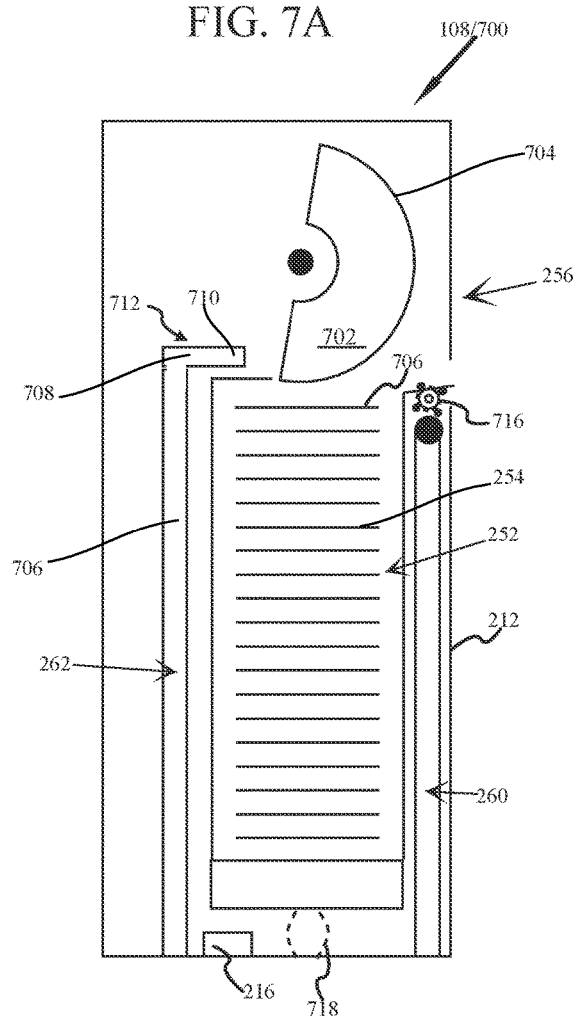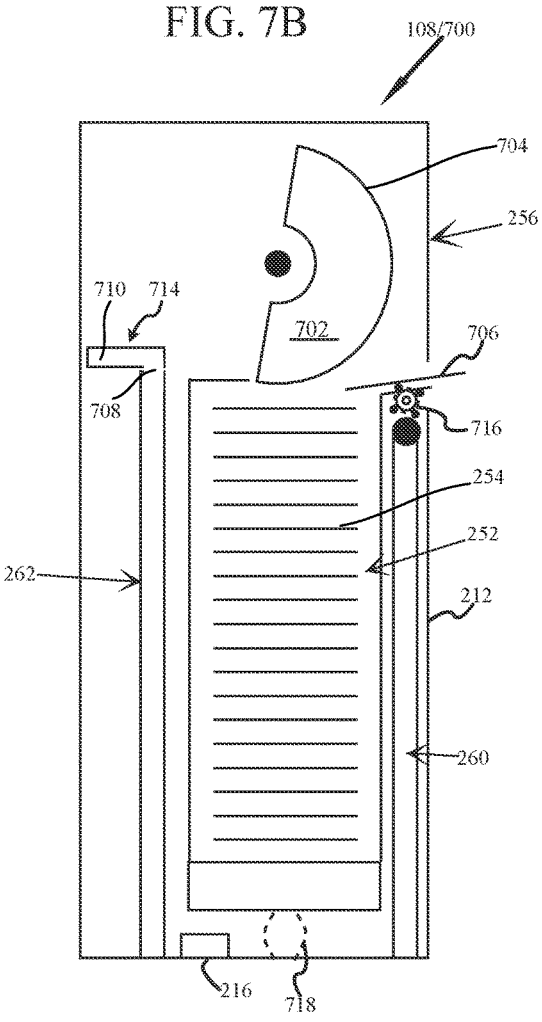

SYSTEM AND METHOD FOR MULTI-MODAL DOSING DEVICE

CROSS REFERENCE TO RELATED APPLICATIONS

This application is a continuation of U.S. patent application Ser. No. 16/726,193 filed Dec. 23, 2019, now U.S. Pat. No. 10,888,665, entitled SYSTEM AND METHOD FOR MULTI-MODAL DOSING DEVICE and incorporated by reference. This continuing application claims the benefit of U.S. patent application Ser. No. 16/726,193 which in turn claimed the benefit under 35 U.S.C. § 119(e) of U.S. Provisional Application Ser. No. 62/787,650 filed Jan. 2, 2019 and entitled MEDICINAL DOSING DEVICE AND SYSTEM, the disclosure of which is incorporated herein by reference.

In addition, the following patent applications are incorporated by reference herein in their entireties: U.S. Patent Application Ser. No. 62/660,974 entitled SMART VAPORIZER AND SYSTEM FOR CONCENTRATE PRODUCTS (hereinafter "'974 App"), U.S. Patent Application Ser. No. 62/721,699 entitled VAPORIZER CARTRIDGE SYSTEM AND METHOD OF USE (hereinafter "'699 App"), U.S. patent application Ser. No. 16/541,062 entitled SYSTEM AND METHOD FOR VAPORIZING CARTRIDGE SYSTEM WITH DIFFUSER (hereinafter "'062 App"), and U.S. patent application Ser. No. 16/559,556 entitled SYSTEM AND METHOD FOR DETERMINING AN APPROPRIATE DOSE OF A PRODUCT (hereinafter "'556 App").

FIELD OF THE INVENTION

The present invention relates generally to a system and method for a medicinal dosing device structured and arranged so as to permit a variety of different modalities for providing a dose of a given product to a user. The product is generally understood to be a medicament or pharmaceutical compound, and the variety of different modalities include, but are not limited to: inhalation, spray, pill or tablet, dropper, dissolvable strip, injection, nebulizer, and/or transdermal gel or ointment. In particular, the present invention presents a system and method for the precise dosing of a product by providing a plurality of different multi dose cartridges structured and arranged for different delivery modalities, the cartridges safe and nonfunctional unless coupled to a control base which is configured to recognize the type of product within the cartridge and control the dosing of the product to a person.

BACKGROUND

Mendicant products may be provided in a variety of different forms—topical spray, topical gel or ointment for absorption through the skin, pills or tablets, dissolvable strips, mist, and vapor, just to name a few. Indeed, the same product may even be available in a variety of different forms permitting a person to select the modality of delivery that he or she finds most effective. Moreover, one person may prefer to swallow a pill while another may prefer an inhalant, while yet another prefers a topical ointment.

Because different delivery modalities may or may not involve additional transport agents—i.e. an oil, cream, dissolvable wax, etc . . . the intended dosage of a product may vary from one modality to another. Although for some ailments, such as poison ivy rash, the issue of dosage may not be of significant concern, this is not always the case.

Indeed, with the increasing proliferation of plant based medicinal products, proper dosage is an important part of patient care for consistent and reliable treatment of a given condition or ailment. Indeed, in some cases different dosages of the same product may be appropriate for different conditions or ailments—thus further emphasizing the importance of proper product dosing for a specific condition or ailment.

Prior art delivery devices, such as vaporizing devices, have often been configured with multi-dosage cartridges or reservoir systems for the vaporization and delivery of a specific compound. Some of these devices are quite complex and involve wireless communication systems and the interaction with other computing system to verify that a person is properly authorized to use the product, the dosage the person should receive, as well as to track their usage and even their feedback regarding the effectiveness of the usage. But such devices are strictly for a given modality of delivery—i.e., inhaled vapor.

Indeed, different modalities for delivery have traditionally required modality specific devices—a pump or squeezable tube for an ointment, a vaporizer, a nebulizer, a pill dispenser, etc . . . . For a person who may have a variety of different ailments or conditions, and therefore desiring different delivery modalities, a plurality of different devices can be both cumbersome and confusing. Further, some devices—such as vaporizers, may be very sophisticated and able to track and adjust dosage, while others may not.

As different devices may be provided by different entities, the methods of hardware and/or software control may vary widely. Further, for smart devices that strive to help manage dosage, devices from different providers may require a user to have multiple accounts, and information in one account may not be shared with another—again permitting the opportunity for inconstant dosing.

Some devices may permit adjustment to the dosage amount, while other devices may not, and still other devices may have no actual dosage control—relying on the person to measure or otherwise assess how much of the product has been dispensed.

Indeed, in some cases for some delivery modalities there may be little if any dosage control leading to both inconsistent administration as well as the possibility for use by unintended persons.

Moreover, a person may have a number of different devices providing the same or different products in a variety of different delivery formats—vapor, tablet, spray, cream, etc . . . , but have little or no idea as to the remaining dosages left in some devices, and/or an effective way to manage his or her dosing administration. Further, a care giver may have no easy or immediate way to review the dosing history across a plurality of different devices for adjustment or confirmation of treatment.

Hence there is a need for a method and system that is capable of overcoming one or more of the above identified challenges.

SUMMARY OF THE INVENTION

Our invention solves the problems of the prior art by providing novel systems and methods to provide controlled dosage delivery across a plurality of delivery modalities.

In particular, and by way of example only, according to at least one embodiment, provided is a multi-modal product dosing system, including: a dosing device provided by temporarily engaging one of a plurality of cartridges to a control base, at least two cartridges having different modality of delivery; the control base characterized by: a housing at least partially enclosing: a cartridge receiver structured and arranged to temporarily engage one of the plurality of different cartridges; a cartridge reader structured and arranged to read identification information from the cartridge; a wireless transceiver structured and arranged for wireless communication with at least one remote computing device; at least one lockout deactivator structured and arranged to disengage at least one lockout mechanism of the cartridge received by the cartridge receiver; a controller structured and arranged to: receive cartridge information from the cartridge reader; detect a dosing event; and communicate, by wireless transceiver, the cartridge information and each detected dosing event to the at least one remote computing device; each of the plurality of cartridges characterized by: a housing at least partially enclosing: a reservoir of product; a dispenser structured and arranged to dispense a predetermined amount of product by a predetermined modality of delivery; a count trigger structured and arranged to indicate each instance of dispensation of the product; at least one data chip structured and arranged to store data regarding the cartridge; a unique identifier associated with the cartridge and the product, the unique identifier structured and arranged to be determined by the control base; and at least one lockout structured and arranged to lockout the dispenser, the at least one lockout disengaged by the control base while the cartridge is temporarily engaged to the control base.

In yet another embodiment, provided is a system for a multi-modal product dosing system, including: a cartridge characterized by: a housing at least partially enclosing: a reservoir of product; a dispenser structured and arranged to dispense a predetermined amount of product by a predetermined modality of delivery; a count trigger structured and arranged to indicate each instance of dispensation of the product; at least one data chip structured and arranged to store data regarding the cartridge; a unique identifier associated with the cartridge and the product, the unique identifier structured and arranged to be determined by a control base; at least one lockout structured and arranged to lockout the dispenser, the at least one lockout disengaged by the control base while the cartridge is temporarily engaged to the control base; wherein the cartridge is temporarily engaged by the control base characterized by: a housing at least partially enclosing: a cartridge receiver structured and arranged to temporarily engage one of a plurality of different cartridges, at least two cartridges having different modality of delivery; a cartridge reader structured and arranged to read identification information from the cartridge; a wireless transceiver structured and arranged for wireless communication with at least one remote computing device; at least one lockout deactivator structured and arranged to disengage the at least one lockout mechanism of the cartridge received by the cartridge receiver; a controller structured and arranged to: receive cartridge information from the cartridge reader; detect a dosing event; and communicate, by wireless transceiver, the cartridge information and each detected dosing event to the at least one remote computing device.

For yet another embodiment, provided is a system for a multi-modal product dosing system, including: a cartridge characterized by: a housing at least partially enclosing: a reservoir of product; a dispenser structured and arranged to dispense a predetermined amount of product by a predetermined modality of delivery; a count trigger structured and arranged to indicate each instance of dispensation of the product; at least one data chip structured and arranged to store data regarding the cartridge; a unique identifier associated with the cartridge and the product, the unique identifier structured and arranged to be determined by a control base; and at least one lockout structured and arranged to lockout the dispenser, the at least one lockout disengaged by the control base while the cartridge is temporarily engaged to the control base.

Further, for another embodiment, provided is a method for multi-modal product dosing, including: providing a control base characterized by: a housing at least partially enclosing: a cartridge receiver structured and arranged to temporarily engage one of the plurality of different cartridges; a cartridge reader structured and arranged to read identification information from the cartridge; a wireless transceiver structured and arranged for wireless communication with at least one remote computing device; at least one lockout deactivator structured and arranged to disengage at least one lockout mechanism of the cartridge received by the cartridge receiver; a controller structured and arranged to: receive cartridge information from the cartridge reader; detect a dosing event; and communicate, by wireless transceiver, the cartridge information and each detected dosing event to the at least one remote computing device; providing a plurality of cartridges, at least two cartridges having different modality of delivery, each cartridge characterized by: a housing at least partially enclosing: a reservoir of product; a dispenser structured and arranged to dispense a predetermined amount of product by a predetermined modality of delivery; a count trigger structured and arranged to indicate each instance of dispensation of the product; at least one data chip structured and arranged to store data regarding the cartridge; a unique identifier associated with the cartridge and the product, the unique identifier structured and arranged to be determined by the control base; at least one lockout structured and arranged to lockout the dispenser, the at least one lockout disengaged by the control base while the cartridge is temporarily engaged to the control base; determining the unique identifier associated with the cartridge upon a selected cartridge being temporarily engaged with the control base; and providing operational settings to the control base for the control of the dispenser in response to the determined unique identifier.

Still for another embodiment, provided is a multi-modal product dosing system, characterized by a control base coupled to one of a plurality of cartridges, at least two cartridges having different modality of delivery, the control base including: a housing at least partially enclosing: a cartridge receiver structured and arranged to temporarily engage one of the plurality of different cartridges; a cartridge reader structured and arranged to read identification information from the cartridge; a wireless transceiver structured and arranged for wireless communication with at least one remote computing device; at least one lockout deactivator structured and arranged to disengage at least one lockout mechanism of the cartridge received by the cartridge receiver; and a controller structured and arranged to: receive cartridge information from the cartridge reader; detect a dosing event; and communicate, by wireless transceiver, the cartridge information and each detected dosing event to the at least one remote computing device; wherein each of the plurality of cartridges is characterized by: a housing at least partially enclosing: a reservoir of product; a dispenser structured and arranged to dispense a predetermined amount of product; a count trigger structured and arranged to indicate each instance of dispensation of the product; at least one data chip structured and arranged to store data regarding the cartridge; a unique identifier associated with the cartridge and the product, the unique identifier structured and arranged to be determined by the control base; and at least one lockout structured and arranged to lockout the dispenser, the at least one lockout disengaged by the control base while the cartridge is temporarily engaged to the control base.

For yet another embodiment, provided is a multi-modal product dosing system, characterized by a control base coupled to one of a plurality of cartridges, at least two cartridges having different modality of delivery, the control base including: a portable housing at least partially enclosing: a cartridge receiver structured and arranged to temporarily engage one of a plurality of different cartridges, at least two cartridges structured and arranged for different modalities of delivery for a product contained therein; a cartridge reader structured and arranged to read identification information from the cartridge; a wireless transceiver structured and arranged for wireless communication with at least one remote computing device; at least one lockout deactivator structured and arranged to disengage at least one lockout mechanism of the cartridge received by the cartridge receiver; a controller structured and arranged to: receive cartridge information from the cartridge reader; detect a dosing event; and communicate, by wireless transceiver, the cartridge information and each detected dosing event to the at least one remote computing device.

For yet still another embodiment, provided is a multi-modal product dosing system, characterized by a control base coupled to one of a plurality of cartridges, at least two cartridges having different modality of delivery, including: a control base characterized by; a portable housing at least partially enclosing: a cartridge receiver structured and arranged to temporarily engage one of a plurality of different cartridges, at least two cartridges structured and arranged for different modalities of delivery for a product contained therein; a cartridge reader structured and arranged to read identification information from the cartridge; a wireless transceiver structured and arranged for wireless communication with at least one remote computing device; at least one lockout deactivator structured and arranged to disengage at least one lockout mechanism of the cartridge received by the cartridge receiver; a controller structured and arranged to: receive cartridge information from the cartridge reader; detect a dosing event; and communicate, by wireless transceiver, the cartridge information and each detected dosing event to the at least one remote computing device; at last one database provided by at least one of the remote computing devices, the database further comprising: user data for each user known to the database; control base data for each control base as related to at least one user known to the database; and product data correlated to one or more unique identifiers known to the database, the unique identifiers further correlated to one or more cartridge, the database permitting correlation of user data to control base data and product data to permit tracking of each product by each user and the product provided by each cartridge; wherein the database further provides at least one operation to add a new user and/or product data to the database.

And for yet another embodiment, provided is a method for multi-modal product dosing system, characterized by a control base coupled to one of a plurality of cartridges, at least two cartridges having different modality of delivery, including: providing a control base characterized by: a housing at least partially enclosing: a cartridge receiver structured and arranged to temporarily engage one of the plurality of different cartridges, at least two cartridges having different modality of delivery; a cartridge reader structured and arranged to read identification information from the cartridge; a wireless transceiver structured and arranged for wireless communication with at least one remote computing device; at least one lockout deactivator structured and arranged to disengage at least one lockout mechanism of the cartridge received by the cartridge receiver; a controller structured and arranged to: receive cartridge information from the cartridge reader; detect a dosing event; and communicate, by wireless transceiver, the the cartridge information and each detected dosing event to the at least one remote computing device; receiving by the control base a selected cartridge having; a housing at least partially enclosing: a reservoir of product; a dispenser structured and arranged to dispense a predetermined amount of product by a predetermined modality of delivery; a count trigger structured and arranged to indicate each instance of dispensation of the product; at least one data chip structured and arranged to store data regarding the cartridge; a unique identifier associated with the cartridge and the product, the unique identifier structured and arranged to be determined by the control base; at least one lockout structured and arranged to lockout the dispenser, the at least one lockout disengaged by the control base while the cartridge is temporarily engaged to the control base; determining the unique identifier associated with the cartridge; transmitting the unique identifier to the remote computing device, the remote computing device querying data records to identify the cartridge and the product contained in the reservoir; transmitting to the controller at least one operational setting to activate the lockout deactivator; and transmitting to the remote computing device a confirmation that a dosage of product has been administered.

BRIEF DESCRIPTION OF THE DRAWINGS AND SUPPORTING MATERIALS

FIGS. 2A-2G illustrates the control base and optional cartridges which when coupled provide a dosing device in accordance with the present invention;

FIGS. 7A-7B illustrates a strip cartridge to be coupled with a control base to provide a dosing device in accordance with the present invention;

DETAILED DESCRIPTION

Figure 1:
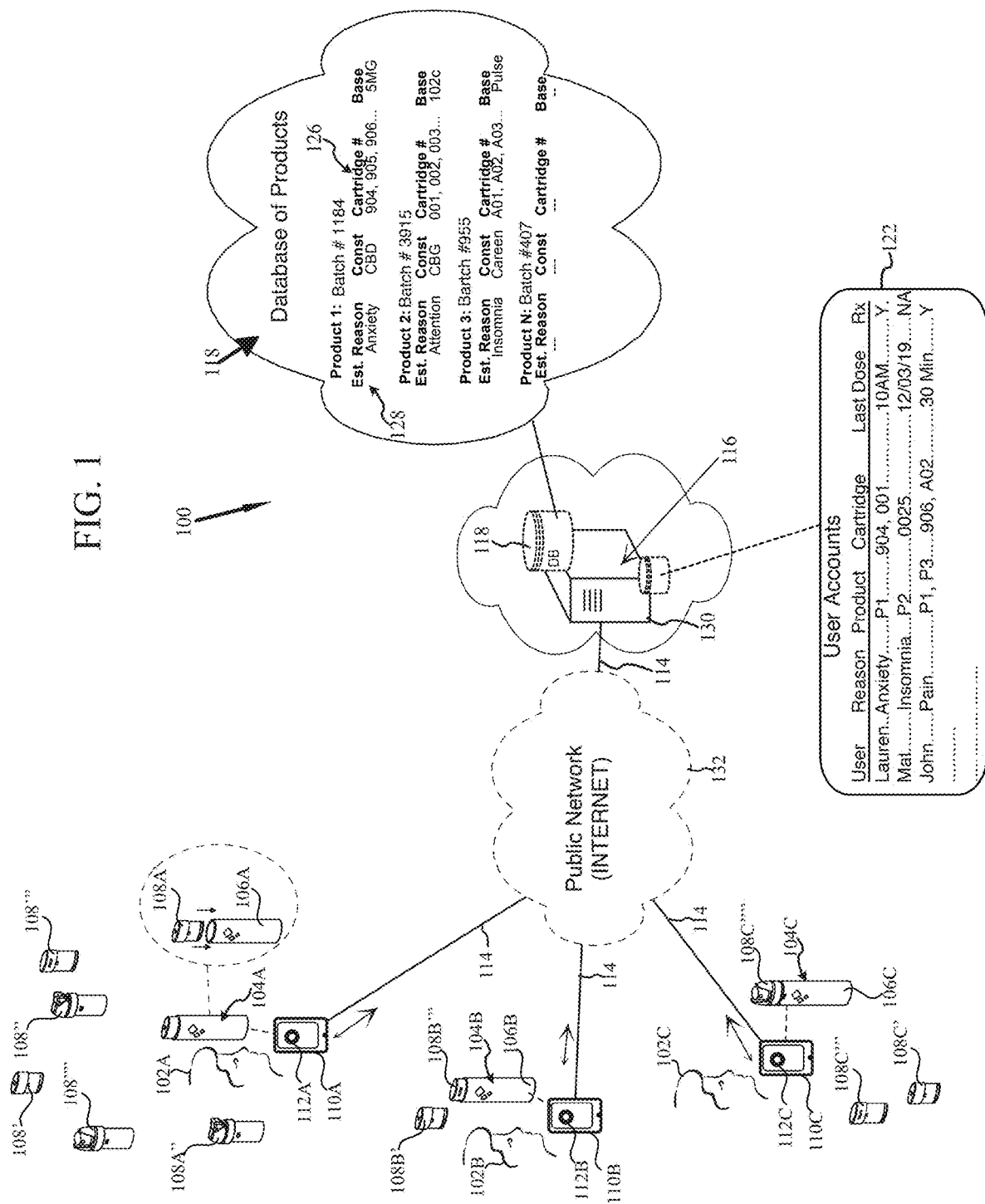
FIG. 1 illustrates a high-level diagram of a system for multi-modal dosing in accordance with the present invention.

Before proceeding with the detailed description, it is to be appreciated that the present teaching is by way of example only, not by limitation. The concepts herein are not limited to use or application with a specific system or method for multi-modal dosing of a product. Thus, although the instrumentalities described herein are for the convenience of explanation shown and described with respect to exemplary embodiments, it will be understood and appreciated that the principles herein may be applied equally in other types of systems and methods for multi-modal dosing of a product as well.

This invention is described with respect to preferred embodiments in the following description with reference to the Figures, in which like numbers represent the same or similar elements. Further, with the respect to the numbering of the same or similar elements, it will be appreciated that the leading values identify the Figure in which the element is first identified and described, e.g., element 100 first appears in FIG. 1.

Various embodiments presented herein are descriptive of apparatus, systems, articles of manufacturer, or the like for systems and methods for multi-modal dosing. In some embodiments, an interface, application browser, window or the like may be provided that allows the user of the computing device to direct behavior of the computing device.

Moreover, some portions of the detailed description that follows are presented in terms of the manipulation and processing of data bits within a computer memory. The steps involved with such manipulation are those requiring the manipulation of physical quantities. Generally, though not necessarily, these quantities take the form of electrical or magnetic signals capable of being stored, transferred, combined, compared and otherwise manipulated. Those skilled in the art will appreciate that these signals are commonly referred to as bits, values, element numbers or other clearly identifiable components.

It is of course understood and appreciated that all of these terms are associated with appropriate physical quantities and are merely convenient labels applied to these physical quantities. Moreover, it is appreciated that throughout the following description, the use of terms such as "processing" or "evaluating" or "receiving" or "outputting" or the like, refer to the action and processor of a computer system or similar electronic computing device that manipulates and transforms the data represented as physical (electrical) quantities within the computer system's memories into other data similarly represented as physical quantities within the computer system's memories.

The present invention also relates to an apparatus for performing the operations herein described. This apparatus may be specifically structured for the required purposes as are further described below, or the apparatus may be a general purpose computer selectively adapted or reconfigured by one or more computer programs stored in the computer upon computer readable storage medium suitable for storing electronic instructions.

To further assist in the following description, the following defined terms are provided.

"User"—typically a person or at the very least a computing device used by a person who is known to the dosing system, or an administration system that is in communication with the dosing system in the sense that he or she has established a user account by providing a threshold of data, e.g. attributes, to identify themselves. Typically, it is expected that the users' interactions with the dosing system or the related administration system will also serve to establish additional attributes about themselves.

"Product"—a compound that may be provided as a liquid, liquid concentrate, edible medium, inhalant, tablet, semi-solid, cream, or other form that may be consumed by a physical person. Generally, this is understood and appreciated to be a plant based medicinal compound. However, it is understood and appreciated that in varying embodiments, a product or products may also be a pharmaceutical, organic, and/or synthetically derived compound. Further still, for yet another embodiment, a product may be provided as a combination of elements selected from the group consisting of, plant, animal, mineral, organic, pharmaceutical, and synthetic compounds.

"Constituent"—an identifiable element of a plant based product, such as, but not limited to a cannabinoid and or a terpene, and various specific forms thereof including, but not limited to a cannabinoid selected from THC, THC-A, CBN, CBG, CBC, CBD, CBD-A, THCV, and CBDV, and a terpene selected from Alpha—Ocimene, Beta-Ocimene, Camphene, Careen, Caryophyllene, Carophyllene oxide, Cymene, Eucalyptol, Isopulefgol, Limonene, Linalool, Myrcene, Pinene, Terpinine, Terpinolene. Moreover, for at least cannabis plant products there are known to be more than 400 different chemical compounds with more than 60 identified as cannabinoid compounds. In varying embodiments, Constituents may also be non-cannabis elements, such as but not limited to psilocybin.

"First Device"—the computing device having at least one processor that is used by the person/User desiring a dosage of a Product for a specified User Reason.

"Dosing System"—The computing system having at least one processor to which users connect when requesting a dose/dosage of a product. The dosing system maintains or at least interacts with a database of products.

"Dosing Device"—the combined and operable assembly provided by a selected one of a plurality of different delivery modality cartridges coupled to a control base, the dosing device operable to provide a metered dose of a product to a user and communicate information regarding the dosage to a remote computing device such as the first device and or dosing system.

"Control Base"—the base component of the dosing device providing power, communication and control features to permit a cartridge to be activated to dispense a metered dose to a user. The control base wirelessly communicates with at first device and/or dosing system to obtain and configure dosing settings such as dose amount and authorization for dosage.

"Cartridge"—one of a plurality of different product dosing components removably coupled by a user to a control base to provide an operable dosing device. Each cartridge provides a reservoir of product and is structured and arranged for a specific modality of delivery for dispensing a metered dose of the product from the reservoir. Dispensation of the product being dependent upon at least the temporary coupling of the cartridge to the control base, and/or activation of the cartridge by the control base.

"Modality of Delivery"—the method of delivery for the product, selected to correspond with the type and nature of the product, and generally understood to be selected from the group consisting of vaporization, inhalation, edible, sublingual, topical, buccal, suppository, and ophthalmic.

"Database"—an indexed set of records correlating products, users, cartridges and control bases. For at least one embodiment, for each product, the database further correlates one or more constituents for each product, established reasons for which products have been used, dosages associated to reasons, and user evaluation feedback. In varying embodiments, user data may include user account information (such as name, age, gender, address, email, phone, etc ...) as well as control bases and cartridges registered to the user, prescriptions for products, doctor or provider contact information, as well as past and present dosage quality and history. In varying embodiments, cartridge data includes the unique identification of each cartridge, identification of the product contained in the cartridge, provider of the product and/or cartridge, initial and/or remaining doses of product within the cartridge, etc. ... The database may also provide operational settings for the control of the cartridge and/or dispenser. Moreover, the database may be one database, or a collection of different databases—such as a database of users and a database of products, but is herein referred to as a single database for ease of discussion and illustration. The database may be established as a relational database and may be localized upon one or more computing systems in a specific location, or distributed such as in a cloud computing space.

With respect to the above defined terms, it is understood and appreciated that for at least one embodiment, each module or system is implemented as a collection of independent electronic circuits packaged as a unit upon a printed circuit board or as a chip attached to a circuit board or other element of a computer so as to provide a basic function within a computer. In varying embodiments, one or more modules may also be implemented as software that adapts a computer to perform a specific task or basic function as part of a greater whole. Further still, in yet other embodiments one or more modules may be provided by a mix of both software and independent electronic circuits.

To briefly summarize, provided is a system and method for multi-modal dosing of products. The system consists principally of a control base to which a user couples a removable cartridge containing the product for dispensation. When the control base is coupled with a cartridge an operable dosing device is fully provided. As is further described below, different cartridges provide different modalities of delivery for product dosage.

As the same control base is used with a plurality of different cartridges having different modalities of delivery, the control base streamlines and simplifies the dosage management as well as record keeping, authorization, feedback and such other elements as may be desired in varying embodiments.

To facilitate dosage management and user record keeping, in general, a user has a smartphone or other portable computing device that has been configured with Internet access and adapted by specific software instructions to perform the specific features and benefits for communicating with the control base of the dosing device, and/or the dosing system in accordance with at least one embodiment of the present invention. More specifically, for at least one embodiment, the user has an application installed upon his or her portable computing device, the application permitting the user to connect with a remote computing system, e.g. the dosing system, with which the user may have established an account and which can provide information regarding the product in the cartridge coupled to the control base, as well as user history, product identity, product history, product manufacturer, dose management settings, constituent makeup of the product, lockout control, and such other data as may be desired in various embodiments.

This summary may be more fully appreciated with respect to the following description and accompanying figures.

Turning now to the drawings, and more specifically, FIG. 1, there is shown a high-level diagram of an embodiment of the System for Multi-modal Dosing of a Product, e.g. SMMDP 100, for users 102 having a dosing device 104 provided by the coupling of a control base 106 to one of a plurality of distinct cartridges 108.

It should be understood and appreciated, that although SMMDP 100 advantageously provides for a plurality of different modalities for delivering a dose of a product, for at least one embodiment only one cartridge 108 may be engaged with the control base 106 at any given time. As is further described below, cartridges 108 that are not engaged with the control base 106 are essentially inert as they are non-functional and will not dispense product in any intended manner.

Moreover, the choice of modality for delivery is determined by the selection of different cartridges 108, the control base 106 providing a consistent and uniform platform for selectively operating the cartridge 108 to dispense the product by the modality desired by the user 102, and tracking data associated with the cartridge 106, the user 102 and the dispensed dose.

As shown, generally each user 102 also has a first computing device 110 having at least one processor and an application 112. For at least one embodiment the application 112 is substantially as the application described in the '556 Application noted above. Each first device 110 is also enabled for network communications 114, such as by wireless network communication. Further still, each first device 110 also has a location determining ability, such as GPS.

For the present example, each first device 110 has been illustrated as a wireless smart phone, but may alternatively be comprised of a portable computer or data assistant device that is capable of portable wireless communication using WiFi networks, wireless network access points, cellular networks, GPS transmissions, and or other such technologies. Moreover, for at least one embodiment, each first device 110 is a smart phone device such as, but not limited to the Apple Computers iPhone® or Samsung Android® device.

For at least one embodiment, each dosing device 104 is operable when assembled as a stand-alone device—which is to say that the dosing device 104 is operable without interaction with one or more remote computing devices, such as a first computing device 110, in the possession of a user 102, or a remote computing system 116 providing a database 118, such as a dosing system 120 as described in the '556 Application noted above.

For yet another embodiment, each dosing device 104 achieves an enhanced operating state when interacting with one or more remote computing devices, such as a first computing device 110 and/or a remote dosing system 120.

Moreover, at least one advantageous aspect of SMMDP 100 relates to the monitoring and control of user dosage across the usage of one or more cartridges 108. Such monitoring and control is advantageously facilitated by the use of a dosing system 120 having at least one database 118 having user data 122 for each user known to the dosing system 120/database 118, control base data 124 for each control base 106 as related to each user 102, cartridge data 126 and product data 128 corelating to one or more unique identifiers to identify products known to the dosing system 120, the unique identity of each cartridge 108 (including for at least one embodiment the modality of delivery and product provided by the cartridge), and such other information as may be desired.

Moreover, although cartridge data 126 and control base data 124 have been illustrated simply as identification values, it is understood and appreciated that these categories, and indeed all data categories can be adapted in varying embodiments to provide additional details/data as may be desired.

For ease of illustration in FIG. 1, the user data 122 has been shown separately from the database 118 which has been illustrated primarily with respect to products and various data elements associated therewith. Indeed, in varying embodiments there may be one unified database that provides all or substantially all of the data relevant for SMMDP 100, or as shown data components such as product data and user data may be divided into separate databases, which may in turn be further provided by different physical computer systems.

It is to be understood and appreciated that the dosing system 120 is a remote system, meaning that it is physically distinct from the first devices 110. Similarly, the database 118, whether a component of the dosing system 120 or another system in communication with the dosing system 120 is distinct and separate from the first devices 110.

Moreover, the dosing system 120 is provided by at least one physical computer system 130 (including at least one microprocessor, memory, I/O device(s) and the like) that is adapted by hardware or software to provide dosing system 120. For an embodiment where the database 118 is a separate system from the dosing system 120 132, the database 118 is also understood and appreciated to be provided by at least one physical computer system (including at least one microprocessor, memory, I/O device(s) and the like) that is adapted by hardware or software to provide database 118.

In varying embodiments, one or more of the elements of SMMDP 100 may be directly connected to one another, if not integrated with each other, but it is understood and appreciated that in most instances the incorporation of the Internet 132 as a common means of communication and information exchange is within the scope of the present invention.

It is also to be understood and appreciated that the elements of the SMMDP 100 need not maintain continual communication links 114—be they physical wire or wireless links. In other words, users 102 may log on or off, and thus establish a link to dosing system 120. Likewise, the dosing system 120, the database 118, and such other network systems and/or devices may be in intermittent connection—connecting when and as necessary for the intended operation of SMMDP 100.

In varying embodiments, the plurality of cartridges 108 may be selected from, but not exclusively limited to, an inhaler carriage, a spray cartridge, a strip delivery cartridge, a gel cartridge, a lotion cartridge, a tablet cartridge, or an injection cartridge. Moreover, different modalities of delivery provide different options for rate of delivery, general vs. targeted delivery, and user comfort during delivery.

For the present example shown in FIG. 1, cartridge 108' is an inhaler cartridge, cartridge 108" is a tablet cartridge, cartridge 108''' is a strip cartridge, and cartridge 108'''' is a spray cartridge.

As inhaled vapor is dissipated into the lungs, the product can enter the blood stream more quickly than may be achieved through a swallowed tablet, or topically applied oil or lotion. Alternatively, a pill, tablet or dermal patch may be desired for time release, while a spray, cream or ointment may be desired for location specific application. An oral spray, eye drop or dissolvable strip may be desired by users who have difficulty with swallowing pills. And injection may be most suitable blood system dispersal or subdural tissue treatment.

An inhaler cartridge 108 is understood and appreciated to provide a dose of product in an inhalant form. Such inhaler cartridges may be provided as vaporizing cartridges wherein a metered dose of the product is vaporized by heat, into a mist suitable for inhalation by a user. An inhaler cartridge may also be provided as a nebulizer which atomizes liquid product into an inhalable gas form, such as by ultrasonic vibration. An inhaler cartridge may also provide a metered dose of product in the form of a fine powder typically disposed into an air flow passage through which a user sucks in air and the dispensed powder. And further, an inhaler cartridge may provide the product in the form of a compressed gas, dispensed in metered bursts to a user. It is further understood and appreciated that inhaler cartridges may provide metered dosage to a user by mouth and/or nose.

For each method of delivery modality, it is to be understood and appreciated that each cartridge 108 is structured and arranged to provide a metered dosage of product—in other words a specifically known quantity of product. For at least one embodiment, some cartridges 108 of SMMDP 100 may be adjusted such that the known dosage may be varied by the user 102, the application adapting the first computing device 110, and/or the dosing system 120. In all cases, dispensation of a metered dosage by any delivery modality permitted by a cartridge 108 is dependent upon the cartridge being properly coupled to the control base 106.

For the present example there are shown a plurality of users 102, of which users 102A 102B, and 102C are exemplary. Each user 102A, 102B, 102C, has a dosing device 104A, 104B, 104C consisting of a control base 106A, 106B, 106C and at least one cartridge 108A, 108B, 108C. As shown, each user 102 has a plurality of different cartridges 108, and as such is afforded an option of selecting different delivery modalities or the product provided by each cartridge 108.

Exemplary dosing device 104 may be more fully appreciated with respect to FIGS. 2A-2E. Moreover, FIG. 2A is a tilted perspective view showing the bottom of control base 106 and the bottom of cartridge 108, FIG. 2B is a top perspective view showing the top of control base 106 and the top of cartridge 108, and FIG. 2C shows the assembled dosing device 104, the cartridge 108 and control base 106 as shown in FIG. 2B now engaged.

The control base 106 has a housing 200 which may further provide buttons 202 and or lights 204 as well as other display components. For at least one embodiment, the base 206 of the control base 106 provides a port 208 that may be used for recharging an internal power supply, and or providing new firmware to the electrical and computing components within the housing 200. Opposite from the base 206, the housing 200 provides an opening 210 structured and arranged to receive any of a plurality of different cartridges 108 compatible with SMMDP 100, at least two of the different cartridges 108 providing different modalities for delivery of products.

The cartridge 108 also provides a housing 212, and as may be appreciated in FIG. 2A, the base 214 of cartridge 108 provides a data chip 216, one or more ports 218 for lockout device control, power contacts 220, dose count communication, and or other elements for the exchange of data or physical control.

The cartridge 108 may also provide a retainer 222 such as a clip, which at least temporarily binds with the inside of control base 106 housing to keep the control base 106 and cartridge 108 engaged. For at least one embodiment, the retainer 222, such as clips are also a lockout. Moreover, as shown, retainer 222 may be cantilevers extending away from the cartridge housing 212. When so deployed, internal elements or linkage (not shown) lockout operation of the cartridge 108. For example, an upper portion of the retainer 222 may engage with a slot, groove or other structure of the dispenser 256 when the retainer 222 is deployed, but when coupled with the control base 106 and therefore pressed in, the retainer(s) 222 not only temporarily bind the cartridge 108 with the control base 108, but the upper portion of the retainer 222 releases from the slot, groove or other structure of the dispenser 256. For at least one embodiment, as these cantilevers are pressed inward, such action also disengages at least one lockout that prevents the cartridge from operating when disconnected from the control base 106. As may be appreciated in FIGS. 2B and 2C, the top of cartridge 108 provides one or more openings 224 from which product is dispensed to the user. In the case of exemplary cartridge 108 shown in FIGS. 2A-2C and 2G, the cartridge is an inhaler cartridge and the openings 224 are vents from which the user may inhale vapor.

Figure 2F:
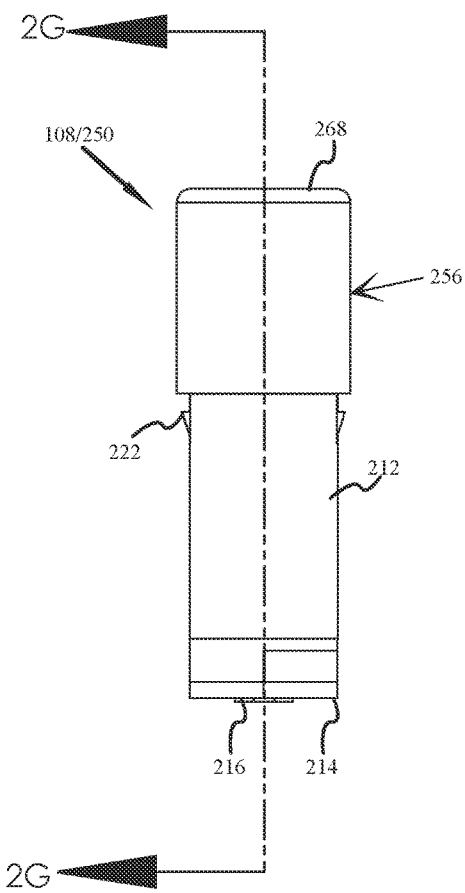
Figure 2G:
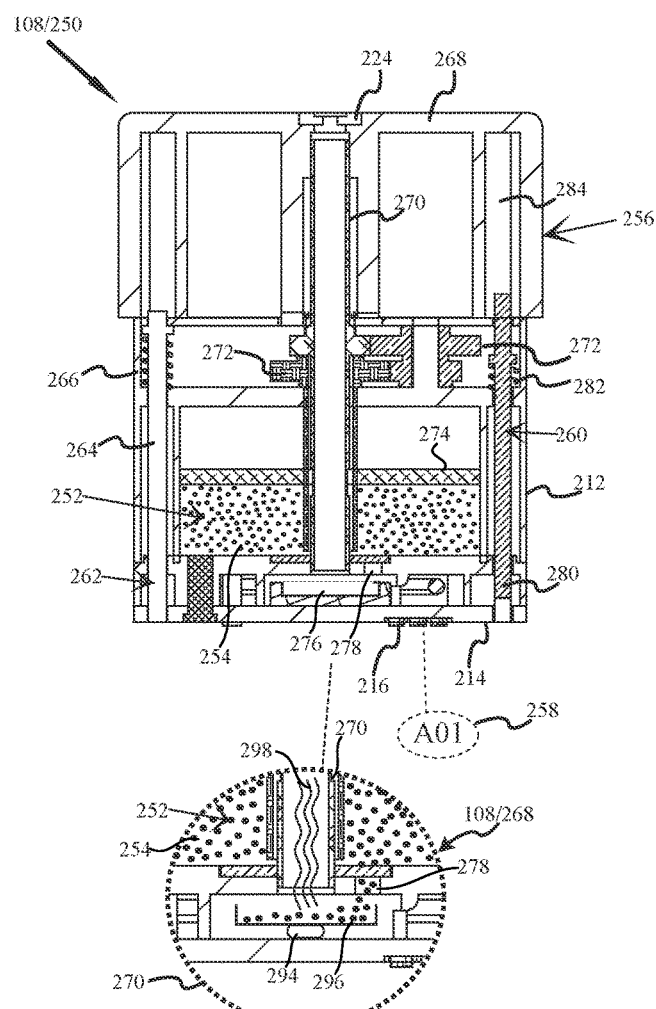

FIGS. 2D and 2E provide a perspective view and cut through view of the control base 106, and FIGS. 2F and 2G provide a perspective view and cut through side view of an exemplary cartridge 108 (enlarged for ease of illustration and discussion). With respect first to FIG. 2E, as shown, for at least one embodiment, the control base is characterized by a housing 200 at least partially enclosing a cartridge receiver 226, a cartridge reader 228, a wireless transceiver 230, a lockout deactivator 232, a controller 234 and a power supply 236 such as a battery.

The cartridge receiver 226 is structured and arranged to temporarily engage one of a plurality of different cartridges 108, and in varying embodiments may provide one or more spring clips, sockets, pins, magnets or other structures configured to engage and temporarily hold the engaged cartridge 108. The cartridge receiver 226 may also provide electrical contacts that engage with corresponding contacts of the cartridge 108 so as to provide power to, and exchange data with, the engaged cartridge 108.

The cartridge reader 228 is structured and arranged to read identification information from the cartridge 108. The identification information may be provided by a variety of different devices such as but not limited to, a smart chip, such an EPROM, EEPROM, or other data chip 216, a QR code, barcode, physical pattern, or other means of encoding identifying information. This identification information may be used to uniquely identify both the cartridge 108 as well as the product contained by the cartridge, such as but not limited to the batch and manufacturer of the product.

The wireless transceiver 230 is structured and arranged for wireless communication with at least one remote computing device. For at least one embodiment, as shown in FIG. 1, the initial remote computing device may be the first device 110 of a user 102, which in turn provides greater communication access, e.g. Internet access, such that the control base 106 may send and receive information to at least one remote computing device providing a database 118. Of course, for some embodiments, the first device 110 may provide caches of database 118 information such that the control base 106 interactions are generally with the first device 110. For yet other embodiments, the wireless transceiver 230 may permit the control base 106 to directly achieve wireless network access to a remote computing device providing a database 118 without requiring a first device 110 as an access point and/or data bridge.

The lockout deactivator 232 is structured and arranged to disengage at least one lockout mechanism of the cartridge 108 received by the cartridge receiver 226. Moreover, for at least one embodiment, the cartridge 108 is in a disabled or locked out state and cannot be used until the at least one lockout has been disengaged. Although the lockout deactivator 232 may alternatively be termed a lockout activator in that it engaged one or more lockout devices, it has been termed herein as a lockout deactivator 232 to help reinforce the advantageous nature of SMMDP 100 not to be used unless authorized. In varying embodiments, the lockout deactivator 232 may be electronic or electromechanical device such as, but not limited to an electrical switch to enable or disable power, a solenoid or geared mechanism operable to apply or remove pressure upon at least a specific component of the cartridge, or other operable element that mechanically, electrically, or magnetically enables or disables the lockout of a cartridge 108 engaged with the control base 106.

Indeed for at least one embodiment, multiple lockout elements may be employed—such as a first lockout device as a cartridge lockout and a second lockout device as a dose control lockout. Moreover, the first lockout may be structured and arranged to disable use of the cartridge when not coupled to the control base, while the second lockout is structured and arranged to permit activation and deactivation when the cartridge is coupled to the control base. As shown and describe above, for at least one embodiment, the retainer 222, e.g. opposing cantilevers extending from either side of the cartridge housing 212 are the external lever elements of a cartridge lockout, such that when they are deployed away from the cartridge 108, the cartridge 108 is mechanically disabled, but when pressed inward, they disengage a first lockout in addition to temporarily binding the cartridge 108 with the control base 106 during use. For design and production reasons, in varying embodiments it may be desired to provide at least these first and second lockout options as different elements.

Moreover, it is an advantageous feature of SMMDP 100 that cartridges 108 can only properly dispense a dose of product when they are coupled to the control base 106. For at least one embodiment, dispensation of a dose of product from the cartridge 108 is also dependent upon other factors, such as but not limited to the user being authorized to receive a dose of the product, that the user is requesting a dosage of the product at an approved time or within an approved window, that the user is requesting a dosage of the product in a permitted location, and/or other such factors as may be determined appropriate for enhanced product dosage management in varying embodiments.

Indeed, embodiments of SMMDP 100 may optionally confirm a variety of factors, such as but not limited to, that the user is the owner or authorized user of the cartridge 108, is of an age for use of the cartridge 108, has a prescription for use of the cartridge 108, has not taken a previous dosage of the same product or another product that would be potentially harmful if combined with the present request for a dosage of product from the cartridge 108, etc . . . . In other words, even when a cartridge 108 has been temporarily engaged with the control base 106, for at least one embodiment the control base 106 will confirm that the user is authorized for the use of the cartridge 106.

The controller 234 is structured and arranged to receive cartridge information from the cartridge reader 228, optionally control the lockout deactivator 232 to permit or deny a dosing event, detect a dosing event, and communicate by the wireless transceiver 230, the cartridge information and each detected dosing event to the at least one remote computing device, such as the user's first device 110 and/or the dosing system 120, specifically the remote computing device providing the database 118.

The controller 234 may also optionally be electrically coupled to one or more lights or display panels and buttons so as to provide visual information to a user and receive commands from a user.

For at least one embodiment the control base 106 may also include a dose counter 238, such as a micro switch that is triggered when each dose is dispensed from the temporarily engaged cartridge 108. For at least one alternative embodiment, the dose counter is a component of the cartridge 108, with each dispensed dose being reported to the control base 106 as well. Further, for at least one alternative embodiment, the cartridge 108 has a display (not shown) which regardless of whether the dose counter is a component of the control base 106 or the cartridge 108, reports the remaining number of doses for the cartridge. Further, this remaining dose count may be observed by a user whether the cartridge 108 is coupled to the control base 106 or not.

The power supply 236, such as a battery provides the electrical power to the control base 106 and, in at least some embodiments, the received cartridge 108. The power supply 236 may be a rechargeable battery, and the housing 200 may further provide a charging port 240 such that the power supply 236 may be replenished without removal from the housing 200.

As noted above, FIGS. 2F and 2G provide a perspective view and side view of an exemplary cartridge 108. For ease of illustration and discussion, the exemplary cartridge 108 is for an inhaler 250, though it will be understood and appreciated that all cartridges 108 for SMMDP 100 share substantially the same components.

More specifically, each cartridge 108 is characterized by a housing 212 that at least partially encloses a reservoir 252 of product 254 (e.g. medicate) and a dispenser 256. The cartridge 108 also provides at least one data chip 216, a unique identifier 258 (may be incorporated in the data chip 216), a lockout 260 and a count trigger 262. As noted above, the product 254 may be a plant based product having one or more constituents which have been, or may be, correlated to the treatment of one or more conditions for which a user may desire a dosage of the product 254.

The housing 212 is structured and arranged so that at least a portion is to be disposed into the housing of the control base 106, and to be received by the cartridge receiver 226 of the control base 106. Common for all cartridges 108, within the housing is at least one reservoir 252 of product 254. The dispenser 256 is structured and arranged to dispense a predetermined amount of product 254, when the cartridge 108 is coupled to the control base 106 and the lockout 260 disengaged.

Moreover, the lockout 260 is structured and arranged to lockout the dispenser 256 when the cartridge 108 is not engaged with the control base 106. As noted above, for at least one embodiment, the controller 234 of the control base 106 has the functional ability to engage and disengage the lockout 260 while the cartridge 108 is coupled to the control base 106. Such optional control advantageously permits SMMDP 100 to enhance dosage management.

Indeed, for at least one embodiment the cartridge 108 has at least two lockout devices, a first lockout component that is disabled upon the cartridge 108 being coupled to the control base 106 and a second lockout component that is activated or deactivated by the controller 234. For example, the first lockout component may be a physical structure such as one or more spring pins within the cartridge 108 that are disengaged by aligned protrusions within the control base 106. The second lockout may be an electrical lockout such as a switch, a screw drive, or a solenoid or gear operated level that is optionally engaged or disengaged as directed by the controller 234. Moreover, for at least one embodiment a first lockout is disengaged by the physical act of the user 102 coupling the cartridge 108 to the control base 106 to provide a desired modality for dosing device 104, while a second lockout is controlled by the controller 234 to advantageously ensure that a proper dosage is only administered to an authorized/permitted user 102. Such authorization/permission may be based on a variety of elements, such as but not limited to, the user being registered with the dosing system 120, the user owning the control base 104 and the cartridge 108, the user having a prescription or other authorization on file with the dosing system, the user being in a physical location where use of the product is permitted, the dosage being requested at a time that free of potential conflict with past administered dosages of the same or different products known to the dosing system 102, etc. . . .

The smart chip 216, or data chip 216, is disposed upon or within the housing 212 in such a location as to be proximate to the cartridge reader 228 when the cartridge 108 is coupled to the control base 106. For at least one embodiment, there may be a direct physical or electrical connection between the cartridge reader 228 and the smart chip 216.

Each cartridge 108 has a unique identifier 258, which may be a physical element such as a QR code, barcode, RFID tag, physical patter or other means of encoding information. The unique identifier 258 serves to uniquely identify each cartridge 108. In addition, the unique identifier may also be used to identify the product 254 within the reservoir, and even more specifically the batch/manufacturer of the product 254. Moreover, for at least one embodiment the unique identifier may have at least two elements—a first portion uniquely identifying the cartridge (e.g. 904) and a second portion that uniquely identifies the product 254 (e.g. 1184). In such fashion, a first cartridge 108 with unique identifier 904-1184 may be distinguished from a second cartridge 108 with unique identifier 905-1184, though both cartridges are also easily recognized to contain the same product 254.

Although the unique identifier 258 may be an established component of the smart chip 216, such as in the case of an EEPROM, the unique identifier is generally understood to be a fixed data element that remains unchanged for the cartridge, while the smart chip 216 is appreciated to be a device which may have additional data added to it, such as remaining dosages, last dosage, or the nature or identification of the product once the cartridge 108 has been filled. Of course, a fixed ID established at the time of manufacturer may be later correlated to the identity of the product later disposed within the cartridge, especially for instances where fabrication of the cartridge 108 occurs prior to the cartridge 108 being filled with product.

It should also be understood and appreciated that the unique identifier 258 may be indexed through a database so as to identify the product 254. Further the unique identifier 258 may be indexed to a user 102, and/or the merchant supplied with the cartridge 108 for sale or distribution.

For at least one embodiment, the unique identifier 258 is a component of the data chip 216, and therefore may not be visible to the user 102. In other embodiments, the unique identifier 258 may be a component of the data chip 216 as well as represented by human readable indicia.

Moreover, for at least one embodiment, the controller 234 is structured and arranged to control the lockout deactivator 232 in accordance with at least the information determined from the cartridge 108, such as the unique identifier 258. In other words, for at least one embodiment the controller 234 is operable to determine from the unique identifier 258 if the cartridge 108 may be activated to dispense a dosage of product 254.

For example, a first user 102A may have his or her control base 106 configured for operation with a first subset of products, while a second user 102B may have his or her control base 106 configured for operation with a second subset of products at least some of which are distinct from the first set of products.

For yet other embodiments, the controller 234 may be configured to recognize only cartridges 108 from the same manufacturer or provider as the manufacturer or provider of the control base 106, or for specific grades or classes of devices—"green" cartridges with "green" control bases, "red" cartridges 108 with "red" control bases 106, "gold" control bases 106 accepting "green" and "red" cartridges 108, etc. . . .

As the unique identifier 258, and/or other data is communicated by the control base to the first device 110 and or the dosing system 120, in varying embodiments, the lockout deactivator 232 is activated or deactivated by the controller 234 in accordance with information received from a remote computing device, such as the first device 110 and/or the dosing system 120. This information from the remote computing system may include, but is not limited to, the user being the owner of the cartridge, the user having a prescription for the product provided by the cartridge, the user requesting the dosage during an approved window or in an approved location, as well as the other conditions described herein or similar thereto.

For at least one embodiment, the controller 234 may deactivate the lockout deactivator 232 for a period of time running from a dosing event. In other words, if the user has just received a dose of product from the dosing device 104, he or she cannot obtain additional doses of product from the current cartridge 108 or another cartridge 108 until a period of time has passed. Such lockout periods may be advantageous to reduce the possibility of overdose, and/or to assist the user in progressively reducing amounts of the product used.

In addition, for at least one embodiment the controller 234 is provided with operational settings for control of the dispenser 256 in response to the unique identifier 258 provided by the cartridge 108. For example, for a vaporizer cartridge 108 the controller 234 may be provided with operational settings for temperature and duration of heating for optimal vaporization of the identified product 254 within the cartridge 108.

The count trigger 262 is structured and arranged to permit counting of each instance of dispensation of the product 254. In varying embodiments, the count trigger 262 may be electronic or electromechanical device such as, but not limited to an electrical switch, a pressure sensor, a hall effect sensor, solenoid, rod, lever or geared mechanism or other operable element that mechanically, electrically, or magnetically indicates to the control base 106 that a dose of product 254 has been dispensed from the cartridge 108.

To summarize the above, for at least one embodiment, provided is multi modal product dosing system 100, including: a dosing device provided by temporarily engaging one of a plurality of cartridges 108 to a control base 106, at least two cartridges having different modality of delivery; the control base 106 characterized by: a housing 200 at least partially enclosing: a cartridge receiver 226 structured and arranged to temporarily engage one of the plurality of different cartridges; a cartridge reader 228 structured and arranged to read identification information from the cartridge 108; a wireless transceiver 230 structured and arranged for wireless communication with at least one remote computing device 116; at least one lockout deactivator 232 structured and arranged to disengage at least one lockout mechanism of a cartridge received by the cartridge receiver 226; a controller 210 structured and arranged to: receive cartridge information from the cartridge reader 228; detect a dosing event; and communicate by the wireless transceiver 230 the cartridge information and each detected dosing event to the at least one remote computing device 116; each of the plurality of cartridges 108 characterized by: a housing 212 at least partially enclosing: a reservoir 252 of product 254; a dispenser 256 structured and arranged to dispense a predetermined amount of product 254 by a predetermined modality of delivery; a count trigger 262 structured and arranged to indicate each instance of dispensation of the product 254; at least one data chip 216 structured and arranged to store data regarding the cartridge 108; a unique identifier 258 associated with the cartridge and the product 254, the unique identifier 258 structured and arranged to be determined by the control base 106; and at least one lockout 260 structured and arranged to lockout the dispenser 256, the at least one lockout 260 disengaged by the control base 106 while the cartridge is temporarily engaged to the control base 106.

Of course, in yet one alterative embodiment, the present invention of SMMDP 100 is embodied primarily in a control base 106 for use with one of a plurality of different cartridges 108 providing optional modalities of delivery.

More specifically, for at least one embodiment, provided is multi modal product dosing system 100, characterized by a control base 106 coupled to one of a plurality of cartridges 108, at least two cartridges having different modality of delivery, the control base 106 including: a housing 200 at least partially enclosing: a cartridge receiver 226 structured and arranged to temporarily engage one of the plurality of different cartridges; a cartridge reader 228 structured and arranged to read identification information from the cartridge 108; a wireless transceiver 230 structured and arranged for wireless combination with at least one remote computing device 116; at least one lockout deactivator 232 structured and arranged to disengage at least one lockout mechanism of a cartridge received by the cartridge receiver 226; and a controller 210 structured and arranged to: receive cartridge information from the cartridge reader 228; detect a dosing event; and communicate by the wireless transceiver 230 the cartridge information and each detected dosing event to the at least one remote computing device 116; wherein each of the plurality of cartridges 108 is characterized by: a housing 212 at least partially enclosing: a reservoir 252 of product 254; a dispenser 256 structured and arranged to dispense a predetermined amount of product 254; a count trigger 262 structured and arranged to indicate each instance of dispensation of the product 254; at least one data chip 216 structured and arranged to store data regarding the cartridge 108; a unique identifier 258 associated with the cartridge and the product 254, the unique identifier 258 structured and arranged to be determined by the control base 106; and at least one lockout 260 structured and arranged to lockout the dispenser 256, the at least one lockout 260 disengaged by the control base 106 while the cartridge is temporarily engaged to the control base 106.

And for yet still another embodiment, the present invention of SMMDP 100 is embodied primarily in plurality of different cartridges 108 providing optional modalities of delivery for use with a control base 106.

More specifically, for at least one embodiment, provided is a system for a multi modal product dosing system 100, including: a cartridge characterized by: a housing 212 at least partially enclosing: a reservoir 252 of product 254; a dispenser 256 structured and arranged to dispense a predetermined amount of product 254 by a predetermined modality of delivery; a count trigger 262 structured and arranged to indicate each instance of dispensation of the product 254; at least one data chip 216 structured and arranged to store data regarding the cartridge 108; a unique identifier 258 associated with the cartridge and the product 254, the unique identifier 258 structured and arranged to be determined by a control base 106; at least one lockout 260 structured and arranged to lockout the dispenser 256, the at least one lockout 260 disengaged by the control base 106 while the cartridge is temporarily engaged to the control base 106; wherein the cartridge is temporarily engaged by a control base 106 characterized by: a housing 212 at least partially enclosing: a cartridge receiver 226 structured and arranged to temporarily engage one of a plurality of different cartridges, at least two cartridges having different modality of delivery; a cartridge reader 228 structured and arranged to read identification information from the cartridge 108; a wireless transceiver 230 structured and arranged for wireless combination with at least one remote computing device 116; at least one lockout 260 deactivator 232 structured and arranged to disengage the at least one lockout mechanism of a cartridge received by the cartridge receiver 226; a controller 210 structured and arranged to: receive cartridge information from the cartridge reader 228; detect a dosing event; and communicate by the wireless transceiver 230 the cartridge information and each detected dosing event to the at least one remote computing device 116.

With the above overview of the general structure of each cartridge 108 now established, specific cartridges for different modalities of delivery may now be more fully appreciated. As noted above, FIGS. 2F and 2G present an inhaler cartridge 108/250. For ease of illustration and discussion, the exemplary inhaler cartridge 250 is a vaporizing inhaler cartridge 250.

The dispenser 256 is provided by a rotating top 268 disposed upon a tube 270. Rotation of the top 268 imparts rotation to the tube 270 which in turn drives gears 272 which impart longitudinal downward motion to plunger 274. This downward motion of the plunger 274 compresses the reservoir 252 of product 254, such that a metered amount of product is dispensed into vaporizing chamber 276 through valve 278. Activated by controller 234, the vaporizing chamber 276 heats the dispensed product to provide a vapor that is inhaled by the user through tube 270.

In varying embodiments, the reservoir 252 and dispenser 256 are substantially as set forth and described in the '062 Application, noted above, with the incorporation of the heating element as a component of the cartridge 108 rather than the control base 106.

Rotation of the top 268 is prevented by lockout 260, achieved by lockout rod 280, which may be engaged by default by spring 282, driving lockout rod 280 into sleeve 284 of top 268. When controller 234 activates lockout deactivator 232, the lockout rod 280 is retracted from sleeve 284 and top 268 is permitted to rotate. In FIG. 2G, lockout rod 280 is shown engaged with sleeve 280 such that the top 268 is prevented from rotating.

In varying embodiments, the mechanism for engagement between the lockout deactivator 232 and the lockout rod 280 is selected from the group consisting of, but not limited to, threaded engagement, magnetic engagement, ball and socket snap. Moreover, an appropriate engagement structure is selected and employed to permit the lockout deactivator 232 of the control base 106 to temporarily engage with the lockout 260 of the cartridge 108, and control the lockout 260 of the cartridge while the control base 106 and cartridge 108 are engaged to provide dosing device 104.

With respect to rotation of the top 268 for dispensation of pre-determined amounts of product 254, in varying embodiments, rotations in increments such as, but not limited to 90 degrees, permitting 90-, 180-, 292- and 360-degree increments may be adopted for 1, 2, 3 and 4 volumes of metered dosage of the contained product 254.

With each increment of rotation, a count trigger 262, such as a rod 264, may be depressed by a nub or other protrusion on the bottom of the rotating top 268 to indicate to the control base 106 that one or more metered doses of product have been dispensed. Spring 266 returns rod 264 to a ready position to await depression during the next rotation of top 268.

With respect to FIG. 2G, although shown and described with respect to an inhaler based on heated vaporization, a nebulizer cartridge 108/290 may be provided by revising the configuration of the vaporizing chamber 276 as shown in the partial enlarged section 292, to provide a piezo-vibrating element 294 proximate to the receiving surface 296 upon which the extruded product 254 is deposited from the reservoir 252. As with the heated vapor, the atomized product 298 is provided through the tube 270 for inhalation by the user.

Figure 3A:
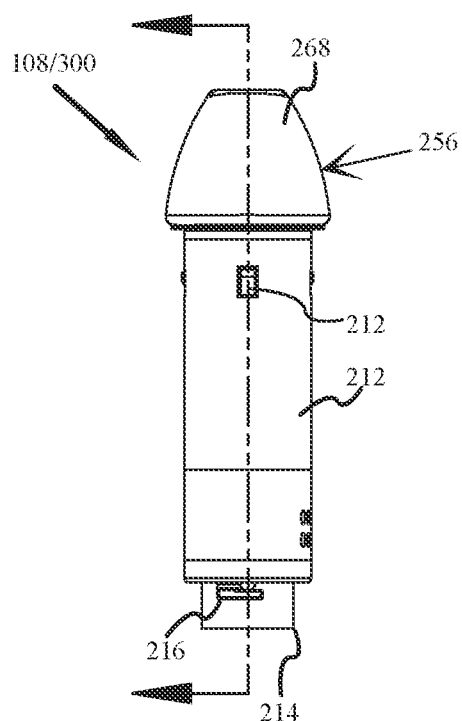
FIGS. 3A-3C illustrates an inhaler cartridge to be coupled with a control base to provide a dosing device in accordance with the present invention.
Figure 3B:
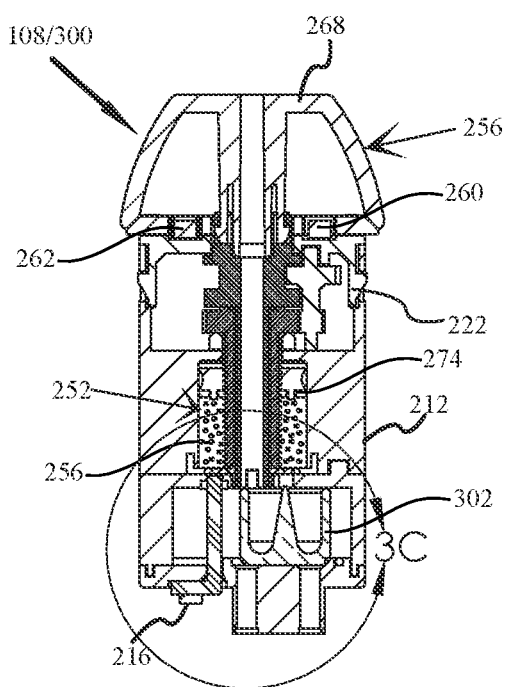
Figure 3C:
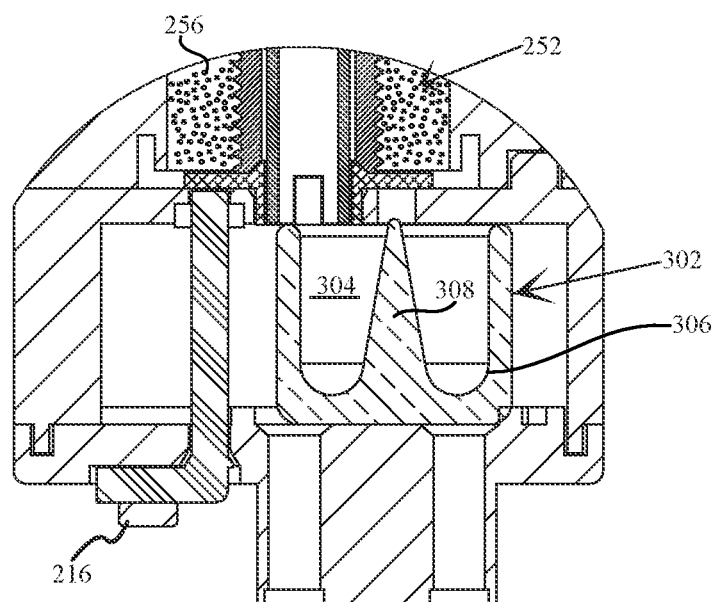

FIGS. 3A, 3B and 3C provide an alternative version for an inhaler cartridge 108/300 of a vaporizing nature. FIG. 3B is a cross sectional view along the side section view shown in FIG. 3A, and FIG. 3C is an enlarged partial section of the heating and vaporizing area 302.

For consistency and relation to the structure of the general cartridge 108, vaporizing cartridge 300 provides a housing 212, a reservoir 252 providing product 254, a dispenser 256 data chip 216 (providing unique identifier 258) lockout 260 and count trigger 262.

More specifically, the vaporizing area 302 is a vaporizing chamber 304 provided by a cavity 306 into which the dispensed product 254 is extruded. This cavity 306 is circumferential with a central rising conical structure 308. The cavity 306 itself is composed of heat conductive material such that the cavity 306, and more specifically the central conical structure 308 provide the heating element to achieve vaporization of the extruded product 254.

In addition, for at least one embodiment the cavity 306 and conical structure 308 are structured and arranged so as to cause a wicking action of the extruded product 254 across their surfaces, and in so doing facilitates a close proximity between the heat source and the extruded product 254. Moreover, the narrow shape of the cavity 306 and the central conical structure 308 advantageously concentrate the extruded product during vaporizing and ensure that extruded material 254 does not dissipate upon non-heating surfaces, thus further advantageously ensuring that the full dose of extruded product is vaporized. In addition, as the cavity 306 is deep, this style of vaporizing chamber is advantageously accommodating to different metered doses of extruded product 254.

For at least one embodiment, either or both the cavity 306 and the conical structure 308 are formed of an oleophilic material or at the very least incorporate oleophilic material upon their surfaces so as to further induce oil-based product 254 to spread out upon their surfaces and thus improve heat transfer and vaporization. For at least one alternative embodiment, wherein the cartridge 108 provides a water-based product 254, either or both the cavity 306 and the conical structure 308 are formed of a hydrophilic material or at the very least incorporate hydrophilic material upon their surfaces.

The exemplary embodiment of inhaler cartridge 108/300 also presents an alternative plunger drive mechanism, more fully shown and described with respect to FIGS. 4A, 4B and 4C below.

For at least the inhalation cartridges 108, e.g., at least exemplary inhaler cartridge 108/250, nebulizer cartridge 108/290, and inhaler cartridge 108/300—and most specifically those cartridges 108 wherein heat is applied to achieve vaporization, it is understood and appreciated that for at least one embodiment the vaporizing chamber 304 is thermally isolated from the reservoir 252, such that heat applied to achieve vaporization does not inadvertently heat, and possibly degrade or alter, the remaining product 254 within the reservoir 252. In addition, for embodiments involving nebulization, the vaporizing chamber 304 (or atomization chamber as it may also be termed) is isolated from the reservoir such that vibrations used to achieve atomization are not inadvertently transmitted to the remaining product 254 within the reservoir 252.

With respect to embodiments for inhalation cartridges 108, e.g., at least exemplary inhaler cartridge 108/250, nebulizer cartridge 108/290, and inhaler cartridge 108/300, the exemplary means for preparing each metered dosage of product 254 in at least one embodiment involves at least partial rotation of the rotating top 268. The translation of rotation about a longitudinal center into lateral motion along the longitudinal center may be achieved by gears and most specifically the angular pitch of threads about the plunger 274. Moreover, for at least one embodiment the drive assembly is based on involute gears—which may include spur, helical and bevel designs. And still further, yet other embodiments may incorporate other intermittent gearing systems for achieving a high gear ratio, such as but not limited to a Geneva mechanism/gear system.

Figure 4C:
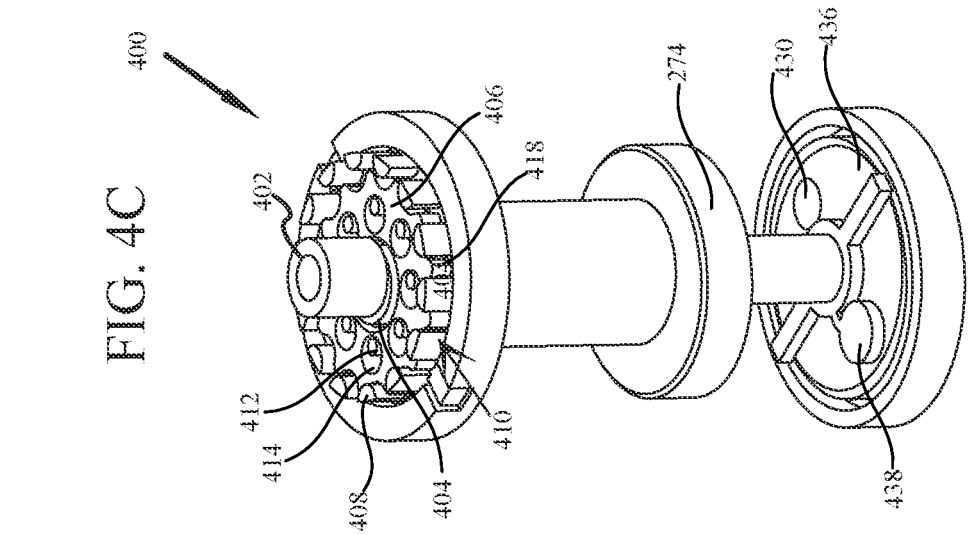
FIGS. 4A-4C illustrates a cartridge incorporating cycloidal gear assembly and metered dose delivery system in accordance with the present invention.
Figure 4B:
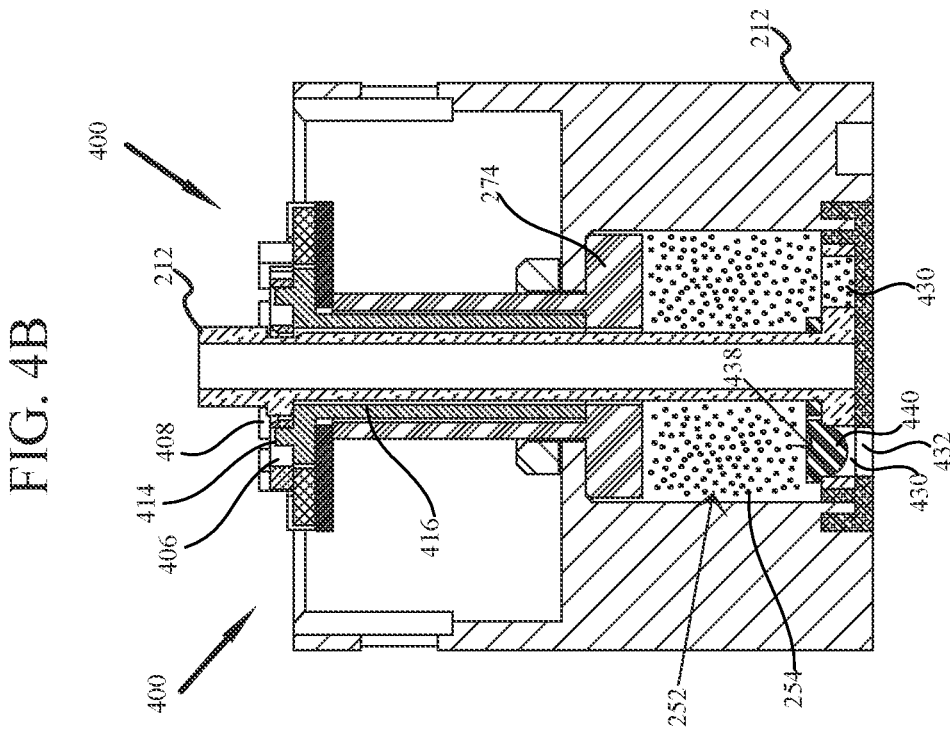
Figure 4A:
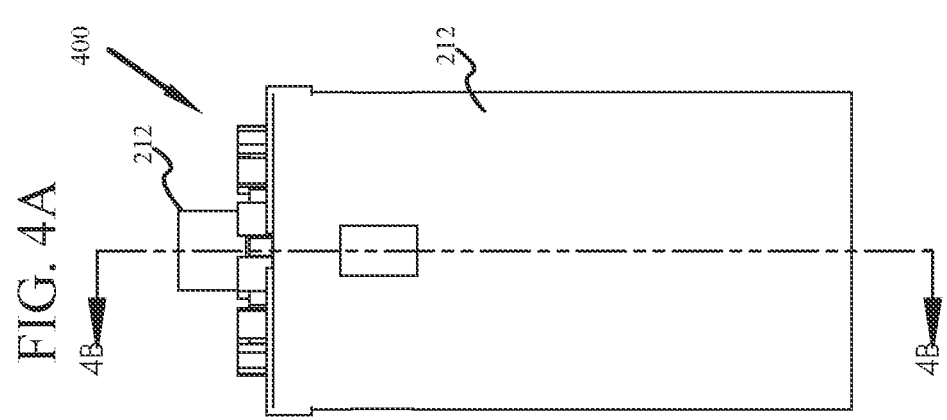

For some embodiments an alternative mechanical structure has been developed incorporating a cycloidal gear assembly 400 as shown in FIGS. 4A-4C. For at least one embodiment, cycloidal gear assembly 400 provides advantageously high gear ratio (e.g. revolutions between the rotating top 268 and the rotation of a shaft to impart lateral motion to the plunger 274, with low friction, high torque, compact size and excellent wear resistance—desirable characteristics facilitating consistent extrusion of product 254 for consistent metered dosing. Moreover, for at least one embodiment, the exemplary inhaler cartridge 108/250, nebulizer cartridge 108/290, inhaler cartridge 108/300, or other cartridge dispensing a liquid, mist, spray, oil, ointment, or other non-solid product 254 wherein the plunger is actuated against the product 254 in a reservoir 252 of cartridge 108, may incorporate a cycloidal gear assembly 400.

More specifically, FIG. 4A shows a side view of a cartridge 108 incorporating cycloidal gear assembly 400, with FIG. 4B presenting a cut through view. FIG. 4C presents a perspective view of the cycloidal gear assembly 400 removed for ease of identification of the components.

Those skilled in the art will appreciate that cycloidal gear assembly 400 is a form of toothed gear assembly based on epicycloid and hypocycloid curves generated by a circle rolling around the outside or inside of another circle. When two toothed gears engage, an imaginary circle—the pitch circle—can be drawn around the center of either gear through the point of contact between their respective teeth. The curves of the teeth outside the pitch circle are known as the addenda and the curves of the tooth spaces inside the pitch circle are known as the dedenda. Moreover, the addendum of one gear rests inside the dedendum of the other gear. The addenda of the wheel teeth are convex epi-cycloidal and the dedenda of the pinion are concave hypocycloidal curves generated by the same generating circle. This ensures that the motion of one gear is transferred to the other at a locally consistent angular velocity.

As is perhaps most easily appreciated in FIG. 4C, the rotating head 268 (shown in FIGS. 2F & 2G or 3A & 3B) is coupled to shaft 402, which in turn is mounted eccentrically to a rolling bearing 404 causing the cycloidal gear 406 to move in a circle. The cycloidal gear 406 independently rotates about the bearing 404 as it is pushed against the ring pins 408 of the outer ring gear 410. As shown, the cycloidal gear 406 has a plurality of apertures 412 each of which receives a roller pin 414 from the output shaft 416 (see FIG. 4B). The apertures 412 are larger in diameter than the diameter of each roller pin 414, and the number of ring pins 410 of the outer ring gear 410 is larger than the number of teeth 418 on the cycloidal gear 406. The roller pins 414 of the output shaft 416 move around in the apertures 412 to achieve steady rotation of the output shaft 416, which in turn is coupled to the plunger 274.

With respect to FIG. 4B, the cycloidal gear assembly 400 drives the plunger 274 to extrude product 254 from the reservoir 252 through ports 430 and 432, which alternate in alignment to an extrusion aperture 434. For at least one embodiment, ports 430 and 432, are substantially identical, the volume of product 254 dispensed determined at least in part by the volume of each port. For the present example, and for ease of illustration and discussion, ports 430 and 432, are shown and described as substantially identical.

More specifically, it will be understood and appreciated that platter 436 is coupled to rotating shaft 402. As such, a rotation of 180 degrees of the shaft is sufficient to transpose the locations of ports 430 and 432, while at the same time driving the cycloidal gear assembly 400 as described above for a precise downward motion of the piston 274. From FIGS. 4B and 4C it will also be appreciated that valve cap 426 remains in a relative position—it does not rotate with platter 432. Valve cap 438 is structured and arranged with a lower section 440 that is dimensioned to substantially fit within either of ports 430 and 432. As the platter 436 is rotated, valve cap 438 will rise out of one port, and plunge into the second upon completion of the 180 rotation, extruding the product 254 from the port (the alighted port 430 or 432) through extrusion aperture 434, and effectively sealing the port (the alighted port 430 or 432) such that only the intended metered dose of product 254 is dispensed.

Figure 5A:
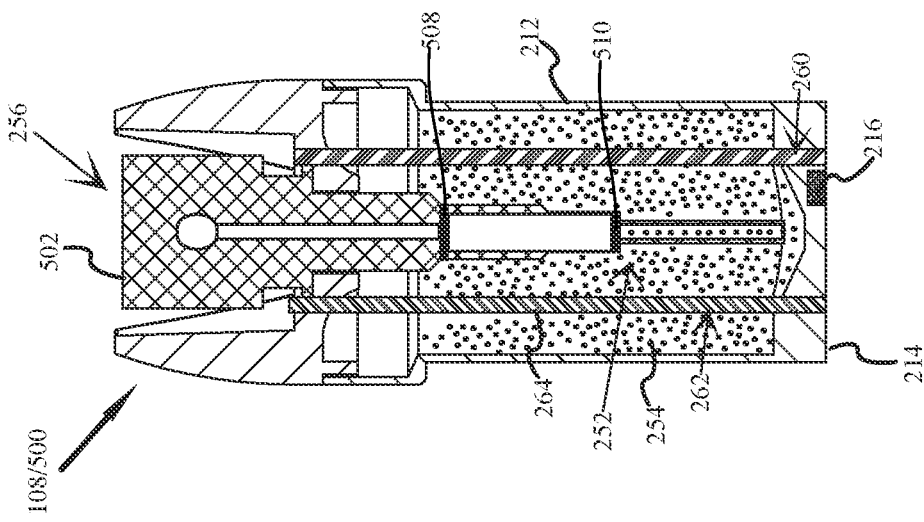
FIGS. 5A-5C illustrates a pump cartridge to be coupled with a control base to provide a dosing device in accordance with the present invention.
Figure 5B:
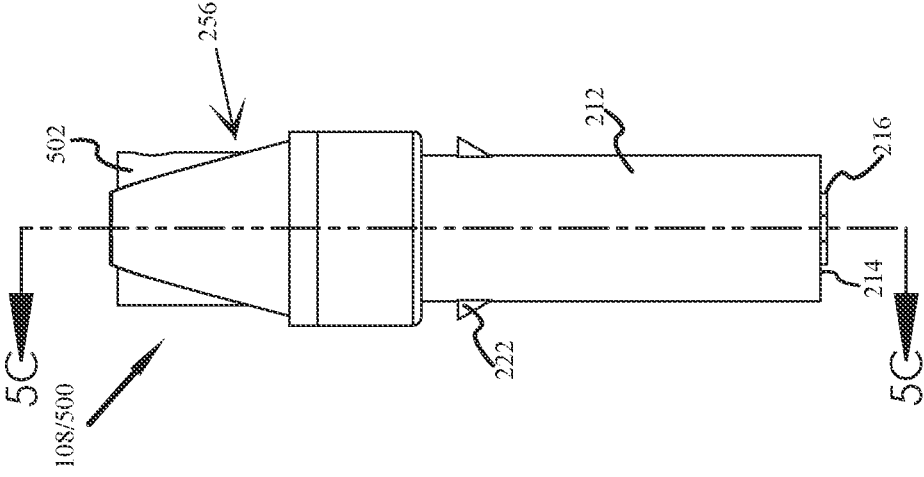
Figure 5C:
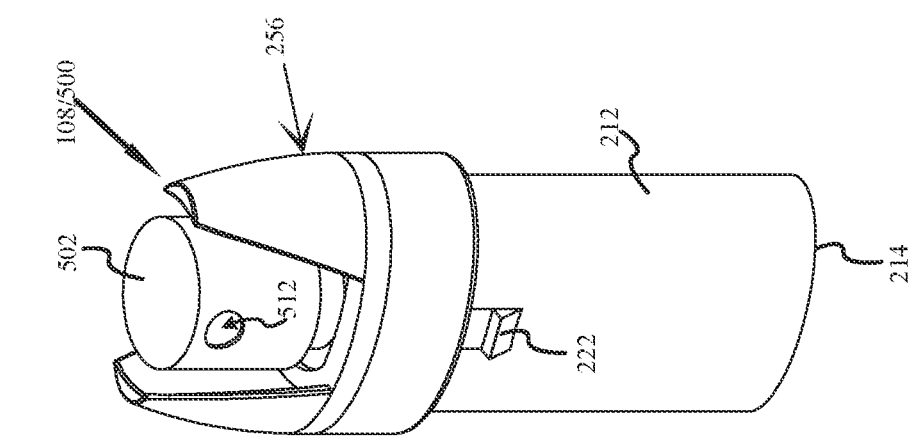

FIGS. 5A, 5B and 5C provide a perspective, side and cut-through illustrations of a conceptual pump cartridge 108/500. Again, for consistency and relation to the structure of the general cartridge 108, pump cartridge 500 provides a housing 212, a reservoir 252 providing product 254, a dispenser 256 data chip 216 (providing unique identifier 258) lockout 260 and count trigger 262.

More specifically, for the pump cartridge 500, the dispenser 256 is provided at least in party by a spring biased pump head 502. For at least one embodiment, the pump shaft 504 incorporates an inner chamber 506 with top 508 and bottom 510 one-way valves, such that upon expansion of the pump shaft 504, liquid product 254 is drawn into the chamber 506, and upon depression of the pump shaft, the product 254 is expelled from the chamber 506 and dispensed through orifice 512 to the user.

For yet another embodiment, the pump cartridge 400 may incorporate an airless pump system substantially similar to that disclosed in the '062 Application.

It will be understood and appreciated that variations in orifice size and internal fluid channels permit varying embodiments of pump cartridge 500 to provide a range of delivery modalities from the extrusion of a gel or lotion to a fine spray. Moreover, in varying embodiment configurations, the pump cartridge 108/500 may be configured as a spray cartridge, a lotion/lotion/paste dispensing cartridge, or a dropper cartridge (such as an eye dropper cartridge).

Figure 6A:
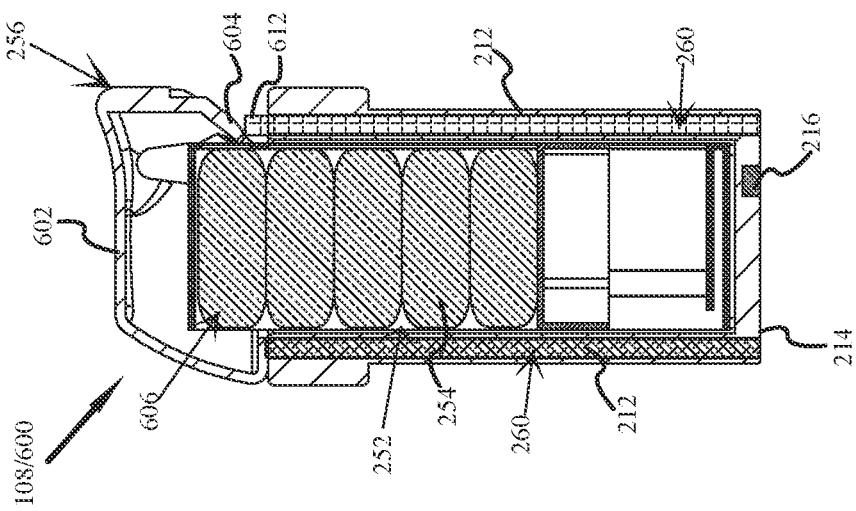
FIGS. 6A-6C illustrates a pill cartridge to be coupled with a control base to provide a dosing device in accordance with the present invention.
Figure 6B:
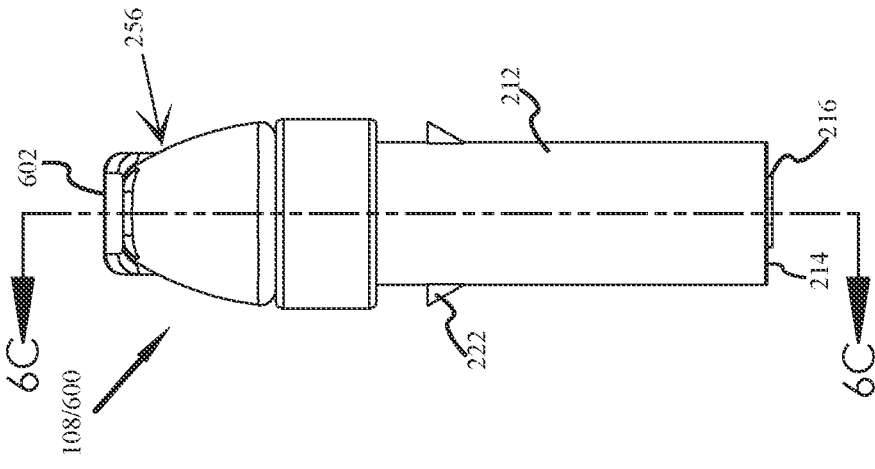
Figure 6C:
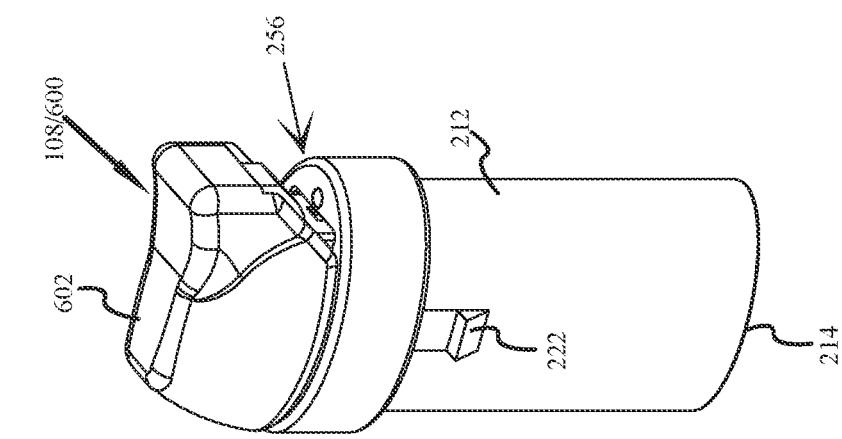

FIGS. 6A, 6B and 6C provide side and cut-through illustrations of a conceptual pill cartridge 108/600. It is to be understood and appreciated that whether described as a pill, tablet, gel cap, capsule or other unit, the pill cartridge 108/600 is structured and arranged to dispense substantially solid pre-fabricated units. The distinction of tablets as formed from compressed powder vs. liquid filled capsules is substantially immaterial, and for the purposes of this discussion, pills or tablets are understood to be interchangeable terms encompassing all such units of products including capsules, gel bodies, severed chunks and the like. More simply stated, pills or tablets as used herein are understood and appreciated to be substantially consistent distinct units of product which do not dissolve into with one another when placed in casual contact.

Once again, for consistency and relation to the structure of the general cartridge 108, pill cartridge 600 provides a housing 212, a reservoir 252 providing product 254, a dispenser 256 data chip 216 (providing unique identifier 258) lockout 260 and count trigger 262.

More specifically, for the pill cartridge 600, the dispenser 256 is provided at least in part by an articulating head 602 disposed over a reservoir 252 of stacked product 254. When the lockout 260 is disengaged, the head 602 is rotated up, such that a dispensing tab 604 is rotated forward to contact and laterally move the top most pill 606 for dispensation to the user 102. As the articulating head is closed, the counting trigger 262 in the form of a rod 608 is depressed, which is registered by the control base 106.

The lockout 260 is similarly provided by an actuated rod 610, shown in lockout position such that the distal end 612 abuts the dispensing tab 604 of the articulating head 602, thereby preventing articulation.

FIGS. 7A and 7B provide conceptual cut through views of a strip cartridge 700. In varying embodiments, the strips 702 may be for sub-lingual consumption, or for temporary adhesion to the skin for transdermal application of the product 254. Again, for consistency and relation to the structure of the general cartridge 108, strip cartridge 700 provides a housing 212, a reservoir 252 providing product 254, a dispenser 256 data chip 216 (providing unique identifier 258) lockout 260 and count trigger 262.

More specifically, for strip cartridge 700, the dispenser 256 is provided by a rotating dispenser pad 704. Having a tacky outer surface 706, as the rotating dispenser pad 702 is brought into contact with the top most strip 702 in the reservoir 252. Upon such contact, the tacky surface 704 will temporarily grip the top most strip 708 and dispense it to the user through a side opening 710.

Strip cartridge 700 has also been illustrated to show at least one alternative for the lockout 260. As shown in FIGS. 7A and 7B, the lockout is achieved by a rotating rod 712, the distal end 714 providing a flange 716. When the rod 712 is rotated to a first position 718, the flange 710 blocks rotation of the dispenser pad 702. As rotation of the dispenser pad 702 cannot be achieved with the flange 716 in this first position 718, lockout is achieved. The lockout 260 is disengaged by rotating the rod 712 to a second position 720, which positioned the flange 716 free of the dispensing pad 702, thus permitting rotation and the dispensation of a strip 702, e.g. top strip 708.

As the top strip 708 is dispensed, roller wheel 716 actuates count trigger 262, and spring 724 presses the stacked product 254 (strips 702) upwards so that the next strip is ready to be dispensed.

Figure 8:
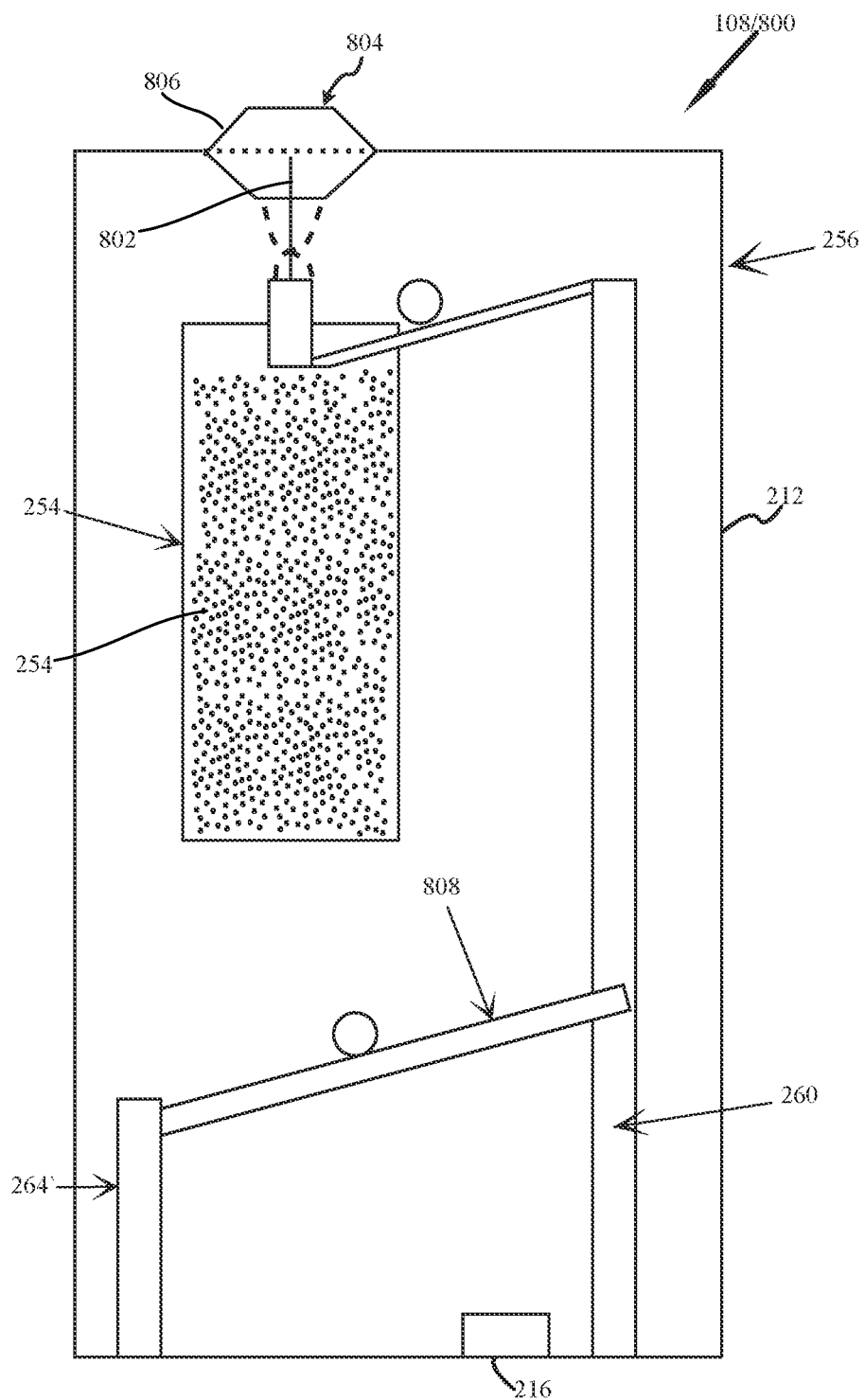
FIG. 8 illustrates an injection cartridge to be coupled with a control base to provide a dosing device in accordance with the present invention.

FIG. 8 provides a conceptual cut through view for an injection cartridge 800. Once again for consistency and relation to the structure of the general cartridge 108, injection cartridge 800 provides a housing 212, a reservoir 252 providing product 254, a dispenser 256, data chip 216 (providing unique identifier 258) lockout 260 and count trigger 262.

More specifically, for the injection cartridge 800, the dispenser 256 is provided at least in part by an injection needle 802 that is actuated through a needle safety feature 804 such as a permeable and cleaning membrane 806. For at least one embodiment, the injection cartridge 800 is a single use cartridge, the product 254 being preloaded for a single dosage. Further, for at least one embodiment, the reservoir 252 is pressurized so as to dispense substantially all of the product in a single, smooth injection.

For at least one alternative embodiment, an internal belt (not shown) of replacement needles 802 may also be incorporated so that each dosage is provided by a new needle 802. Preparation of the dose of product 254 for injection may be achieved as described above with respect to plunger extrusion or pump extrusion, or pressurized gas. Further, lockout 260 may be achieved in a variety of optional ways, including, but not limited to internal mechanical linkage 808 which elevates the needle 802 through the safety feature 804 and triggers the count trigger 262.

Having described embodiments for SMMDP 100 as shown with respect to FIGS. 1-8, other embodiments relating to at least one method for providing multi-modal dosing will now be discussed with respect to FIG. 9 in connection with FIGS. 1-8. It will be appreciated that the described method need not be performed in the order in which it is herein described, but that this description is merely exemplary of one method of multi-modal dosing in accordance with the present invention.

Figure 9:
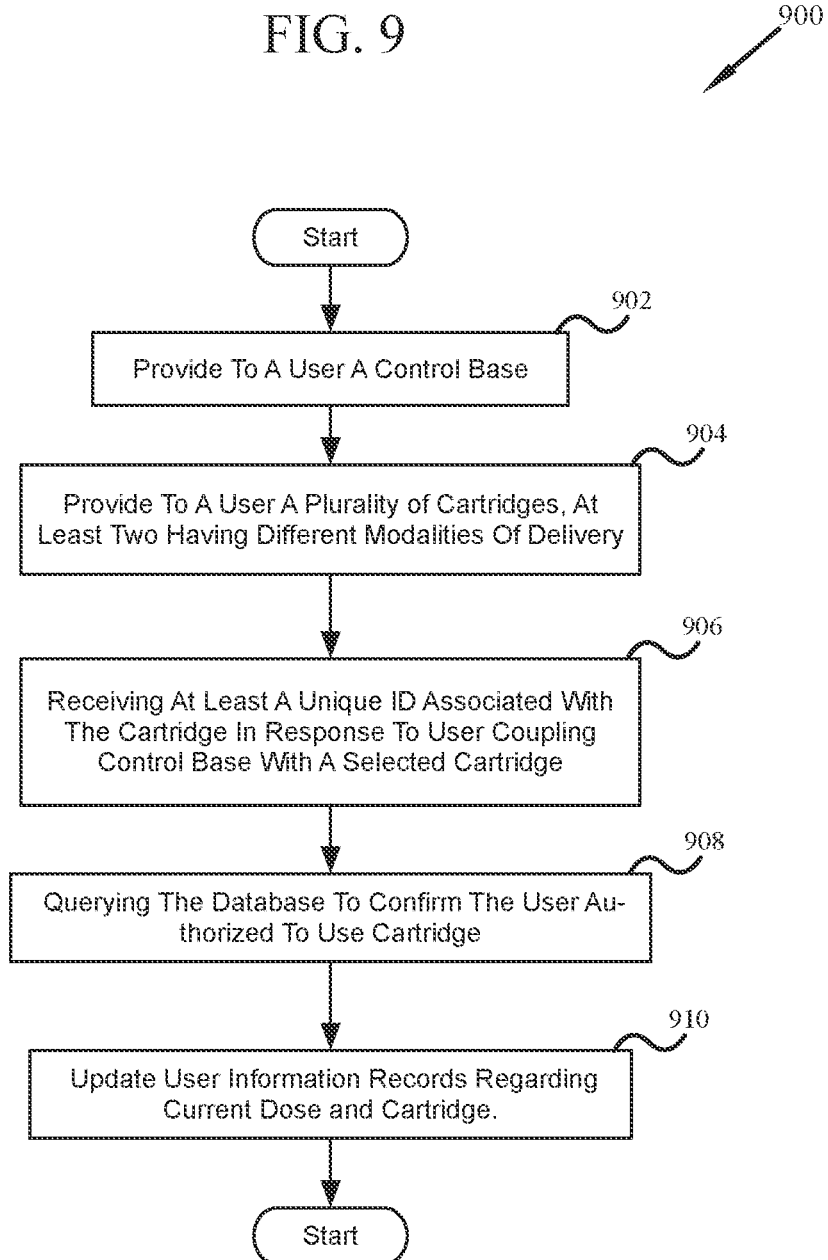
FIG. 9 illustrates a flow diagram for multi-modal dosing in accordance with the present invention.

As shown in FIG. 9, method 900 typically begins with providing a control base 106, block 902. The control base 106 characterized by: a housing 200 at least partially enclosing: a cartridge receiver 226 structured and arranged to temporarily engage one of a plurality of different cartridges; a cartridge reader 228 structured and arranged to read identification information from the cartridge; a wireless transceiver 230 structured and arranged for wireless communication with at least one remote computing device; a lockout deactivator 232 structured and arranged to disengage a lockout 260 mechanism of a cartridge 108 received by the cartridge receiver 202; a controller 234 structured and arranged to: receive cartridge information from the cartridge reader 228; detect a dosing event; and communicate by the wireless transceiver 230 the cartridge information and each detected dosing event to the at least one remote computing device.

The method continued by providing a plurality of different cartridges 108, at least two cartridges 108 providing different modalities of delivery for a product contained within each cartridge, block 904. Even with different modalities of delivery, each cartridge 108 is characterized by: a housing at least partially enclosing: a reservoir 252 of product 254; a dispenser 256 structured and arranged to dispense a predetermined amount of product 254; a count trigger 262 structured and arranged to indicate each instance of dispensation of the product 254; at least one data chip 216 structured and arranged to store data regarding the cartridge; a unique identifier 236 associated with the cartridge 108 and the product 254, the unique identifier 258 structured and arranged to be determined by the control base 106; a lockout 260 structured and arranged to lockout the dispenser 256, the lockout 260 disengaged by the control base 106 while the cartridge is temporarily engaged to the control base 106.

The method 400 continues with the user 102 selecting a cartridge to provide the modality of delivery desired for the intended product. The selected cartridge 108 and the control base 106 are then coupled together to provide dosing device 104.

For at least one alternative embodiment, the user may use his or her first computing device 110, and more specifically the application 112 configuring the first computing device 110 to specify an ailment/condition, i.e. a reason, for which they are requesting a dose of product 254. As the database 118 contains user data, which may include records for the different cartridges 108 in the possession of the user. If the user 102 does not have product 254 suitable for their reason, as set forth in '556 App noted above, the dosing system 120 may also inform the user 102 of the location where the user can obtain appropriate product 254. Further, for at least one embodiment, the dosing system 120 of SMMDP 100 can advantageously suggest the optimal modality of delivery for product 254 suitable for the user specified reason. More simply stated, for at least one embodiment, SMMDP 100 advantageously informs the user of which cartridge 108 provides the modality of delivery that is most appropriate for the user stated reason.

When the cartridge 108 is received within the control base 106 the data chip 216 of the cartridge 108 is read and at least the unique identifier 258 for the cartridge is obtained. The dosing device 104, and more specifically the control base 106, may communicate with at least one remote computing device, and based on one or more identifiers received from the cartridge (i.e. the unique identifier and/or additional data regarding the product) and compared to the database 118.

Moreover, the method continues with receiving at least the unique identifier 258 from the dosing device 104, block 906, and querying the database to determine that the user is authorized to use the cartridge 108, block 908. The database may also provide dispensation data, such as dosage amount, heating characteristics, or other information for use by the control base for advantageously optimized dispensation of the product by the user selected modality.

If the user 102 is authorized, then the control base 106 disengages the lockout 260 via the lockout deactivator 232 and the user is permitted to receive a dosage of the product 254 in the delivery modality provided by the cartridge 108. If the user is not authorized, then the control base does not disengage the lockout 260 and the user is prevented from receiving a dosage of product 254. For at least one embodiment, if the user 102 is not authorized, he or she is informed of this fact as the basis for the requested dosage of product 254 being denied.

Information regarding the dosage dispensed, such as, but not limited to the time, date, and quantity of dosage are reported to the database 118 and recorded with respect to the user data and/or cartridge data, block 910. As the control base 106 is operational with SMMDP 100 with all intended cartridges 108, the use of different cartridges and/or different product is advantageously monitored and recorded.

Substantially real time feedback from users, such as, but not limited to their assessment of effectiveness for the product for a given reason for requesting a dosage of the product may also be captured and recorded—and used to correlate the constituents of the product to such a given reason so as to increase accuracy of suggested/prescribed products in the future.

To summarize, for at least one embodiment provided is a method for multi modal product dosing, including: providing a control base 106 characterized by: a housing 200 at least partially enclosing: a cartridge receiver 226 structured and arranged to temporarily engage one of the plurality of different cartridges; a cartridge reader 228 structured and arranged to read identification information from the cartridge 108; a wireless transceiver 230 structured and arranged for wireless communication with at least one remote computing device 116; at least one lockout deactivator 232 structured and arranged to disengage at least one lockout mechanism of a cartridge received by the cartridge receiver 226; a controller 210 structured and arranged to: receive cartridge information from the cartridge reader 228; detect a dosing event; and communicate by the wireless transceiver 230 the cartridge information and each detected dosing event to the at least one remote computing device 116; providing a plurality of cartridges 108, at least two cartridges having different modality of delivery, each cartridge characterized by: a housing 212 at least partially enclosing: a reservoir 252 of product 254; a dispenser 256 structured and arranged to dispense a predetermined amount of product 254 by a predetermined modality of delivery; a count trigger 262 structured and arranged to indicate each instance of dispensation of the product 254; at least one data chip 216 structured and arranged to store data regarding the cartridge 108; a unique identifier 258 associated with the cartridge and the product 254, the unique identifier 258 structured and arranged to be determined by the control base 106; at least one lockout 260 structured and arranged to lockout the dispenser 256, the at least one lockout 260 disengaged by the control base 106 while the cartridge is temporarily engaged to the control base 106; determining the unique identifier 258 associated with the cartridge upon a selected cartridge being temporarily engaged with the control base 106; and providing operational settings to the control base 106 for the control of the dispenser 256 in response to the determined unique identifier 258.

For yet another embodiment, the method may be summarized as a method for multi modal product dosing system 100, characterized by a control base 106 coupled to one of a plurality of cartridges 108, at least two cartridges having different modality of delivery, including: providing a control base 106 characterized by: a housing 200 at least partially enclosing: a cartridge receiver 226 structured and arranged to temporarily engage one of the plurality of different cartridges, at least two cartridges having different modality of delivery; a cartridge reader 228 structured and arranged to read identification information from the cartridge 108; a wireless transceiver 230 structured and arranged for wireless communication with at least one remote computing device 116; at least one lockout deactivator 232 structured and arranged to disengage at least one lockout mechanism of a cartridge received by the cartridge receiver 226; a controller 210 structured and arranged to: receive cartridge information from the cartridge reader 228; detect a dosing event; and communicate by the wireless transceiver 230 the cartridge information and each detected dosing event to the at least one remote computing device 116; receiving by the control base 106 a selected cartridge having; a housing 212 at least partially enclosing: a reservoir 252 of product 254; a dispenser 256 structured and arranged to dispense a predetermined amount of product 254 by a predetermined modality of delivery; a count trigger 262 structured and arranged to indicate each instance of dispensation of the product 254; at least one data chip 216 structured and arranged to store data regarding the cartridge 108; a unique identifier 258 associated with the cartridge and the product 254, the unique identifier 258 structured and arranged to be determined by the control base 106; at least one lockout 260 structured and arranged to lockout the dispenser 256, the at least one lockout 260 disengaged by the control base 106 while the cartridge is temporarily engaged to the control base 106; determining the unique identifier 258 associated with the cartridge 108; transmitting the unique identifier 258 to the remote computing device 116, the remote computing device 116 querying data records to identify the cartridge and the product 254 contained in the reservoir 252; transmitting to the controller 210 at least one operational setting to activate the lockout deactivator 232; and transmitting to the remote computing device 116 a confirmation that a dosage of product 254 has been administered.

Figure 10:
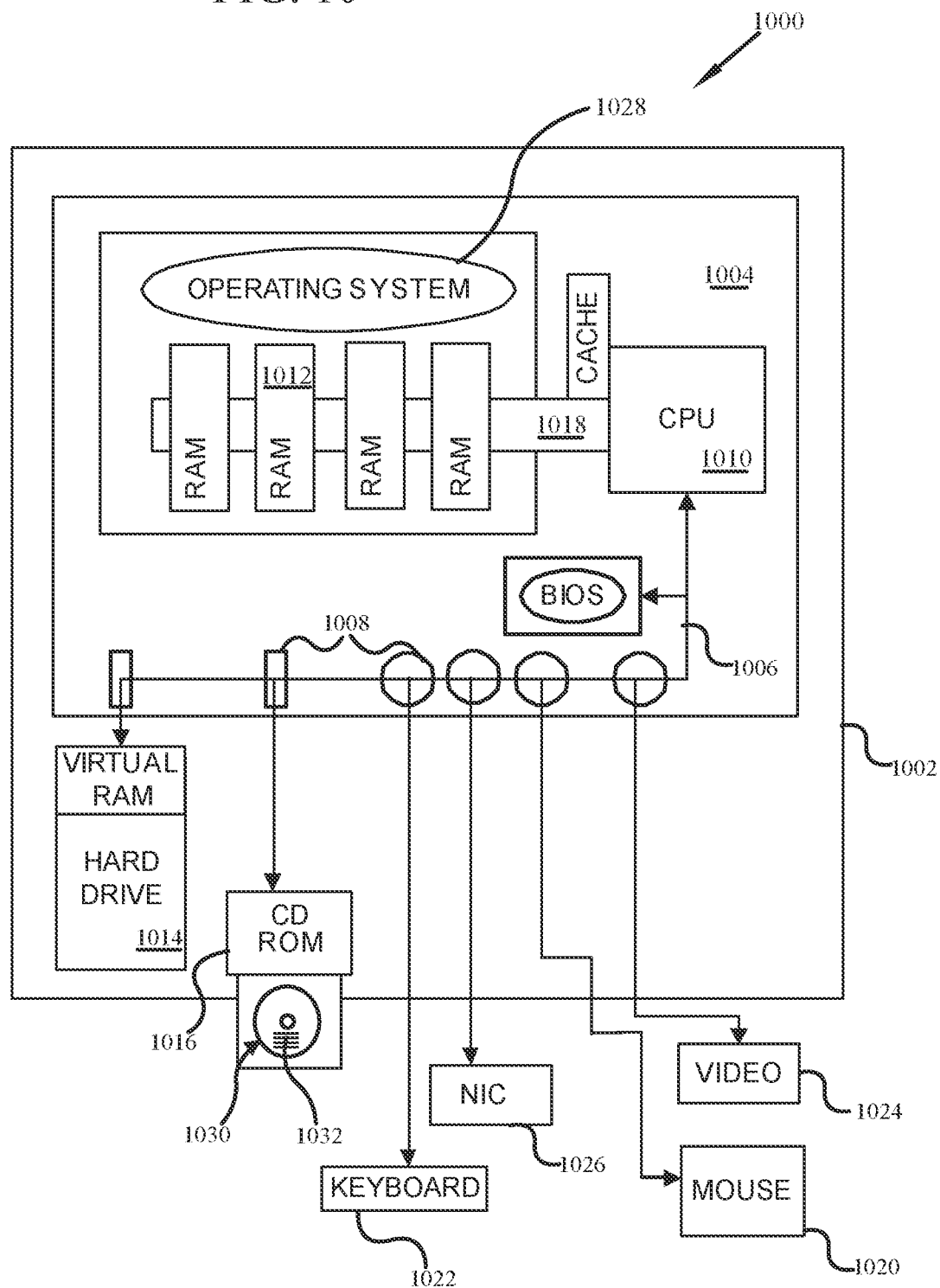
FIG. 10 is a high level block diagram of a computer system in accordance with at least one embodiment.

To expand upon the initial suggestion of at least the first device 110, dosage device 104 (more specifically, the control base 106), dosing system 120, database 118 and other systems comprising SMMDP 100 being computer systems adapted to their specific roles, FIG. 10 is a high level block diagram of an exemplary computer system 1000 such as may be provided for one or more of the elements comprising at first device 110, dosage device 104 (more specifically, the control base 106), dosing system 120, database 118 whether provided as distinct individual systems or integrated together in one or more computer systems.

Computer system 1000 has a case 1002, enclosing a main board 1004. The main board 1004 has a system bus 1006, connection ports 1008, a processing unit, such as Central Processing Unit (CPU) 1010 with at least one microprocessor (not shown) and a memory storage device, such as main memory 1012, hard drive 1014 and CD/DVD ROM drive 1016.

Memory bus 1018 couples main memory 1012 to the CPU 1010. A system bus 1006 couples the hard disc drive 1014, CD/DVD ROM drive 1016 and connection ports 1008 to the CPU 1010. Multiple input devices may be provided, such as, for example, a mouse 1020 and keyboard 1022. Multiple output devices may also be provided, such as, for example, a video monitor 1024 and a printer (not shown). As computer system 1000 is intended to be interconnected with other computer systems in the CSE 100 a combined input/output device such as at least one network interface card, or NIC 1026 is also provided.

Computer system 1000 may be a commercially available system, such as a desktop workstation unit provided by IBM, Dell Computers, Gateway, Apple, or other computer system provider. Computer system 1000 may also be a networked computer system, wherein memory storage components such as hard drive 1014, additional CPUs 1010 and output devices such as printers are provided by physically separate computer systems commonly connected in the network.

Those skilled in the art will understand and appreciate that the physical composition of components and component interconnections are comprised by the computer system 1000, and select a computer system 1000 suitable for one or more of the computer systems incorporated in the formation and operation of CSE 100.

When computer system 1000 is activated, preferably an operating system 1028 will load into main memory 1012 as part of the boot strap startup sequence and ready the computer system 1000 for operation. At the simplest level, and in the most general sense, the tasks of an operating system fall into specific categories, such as, process management, device management (including application and User interface management) and memory management, for example. The form of the computer-readable medium 1030 and language of the program 1032 are understood to be appropriate for and functionally cooperate with the computer system 1000.

Moreover, variations of computer system 1000 may be adapted to provide the physical elements of one or more components comprising each first device 110, dosage device 104 (more specifically, the control base 106), dosing system 120, database 118, the switches, routers and such other components as may be desired and appropriate for the methods and systems for determining an appropriate dose of a product as set forth above.

Changes may be made in the above methods, systems and structures without departing from the scope hereof. It should thus be noted that the matter contained in the above description and/or shown in the accompanying drawings should be interpreted as illustrative and not in a limiting sense. Indeed, many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A multi-modal product dosing system with cross-modality tracking and lockout, characterized by a control base having a housing at least partially enclosing a cartridge receiver, a cartridge reader, at least one lockout deactivator, a wireless transceiver and a controller structured and arranged to operate the cartridge reader, the at least one lockout deactivator and the wireless transceiver to communicate information with at least one remote computing device, the control base structured and arranged to couple to one of a plurality of different cartridges, each cartridge remaining at least partially external to the housing of the control base and at least two cartridges having different modalities of delivery for a product contained therein, each of the plurality of cartridges characterized by:
  a housing at least partially enclosing:
    a reservoir of product;
    a dispenser structured and arranged to dispense a predetermined amount of product by a predetermined modality of delivery, at least a portion of the dispenser external to the housing of the control base;
    at least one data chip structured and arranged to store data regarding the cartridge;
    a unique identifier associated with the cartridge and the product, the unique identifier structured and arranged to be determined by the control base; and
    at least one lockout mechanism structured and arranged to lockout the dispenser to prevent dispensation of the product even when the cartridge is coupled to the control base, unless the lockout mechanism of the cartridge is disengaged by the lockout deactivator of the control base, and wherein activation of any cartridge following a completed administration of product is inhibited unless authorized.

2. The system of claim 1, wherein one of the plurality of different cartridges is selected from a group consisting of: an inhalation cartridge, a topical spray cartridge, a topical liquid dropper, a strip delivery cartridge, a topical gel cartridge, a tablet cartridge, and an injection cartridge.

3. The system of claim 1, wherein the dispenser of one of the plurality of different cartridges further includes a cycloidal gear assembly to actuate a plunger against the reservoir of product to extrude a metered dose of product.

4. The system of claim 1, wherein a first lockout mechanism of the at least one lockout mechanism is structured and arranged as a cartridge lockout and a second lockout mechanism of the at least one lockout mechanism is structured and arranged as a dose lockout.

5. The system of claim 1, wherein at least one of the plurality of different cartridges further includes a vaporizing chamber structured and arranged to receive a metered dose of product from the reservoir, the reservoir thermally isolated from the vaporizing chamber.

6. The system of claim 1, further including a count trigger structured and arranged to indicate each instance of dispensation of the product.

7. The system of claim 1, wherein at least one of the at least one remote computing devices provides a database, the database further comprising:
user data for each user known to the database;
control base data for each of the control bases as related to at least one user known to the database;
product data correlated to one or more unique identifiers known to the database, the at least one unique identifiers further correlated to one or more of the plurality of different cartridges;
the database permitting correlation of the user data to the control base data and the product data to permit tracking of each product by each user and the product provided by each cartridge;
wherein the database further provides at least one operation to add a new user and/or product data to the database.

8. The system of claim 7, wherein the database further provides operational settings for control of the dispenser in response to the unique identifier associated with the engaged cartridge identified by the control base.

9. The system of claim 7, wherein the database further provides authorization for use of the cartridge in accordance with at least one element selected from the group consisting of: the user's location, the user being authorized to receive the dose, the user requesting the dose at an approved time, the user requesting the dose within an approved time window, the user being an authorized user of the dosing device, the user being a registered owner of the cartridge.

10. The system of claim 7, wherein authorization for the control base lockout deactivator to disengage the lockout device of the cartridge temporarily coupled thereto is based at least in part on wireless communication with the database to determine whether a dose has been administered from any cartridge, and to automatically inhibit activation of any other cartridge until a subsequent authorization is received.

11. The system of claim 1, wherein the dispenser is a mechanical device.

12. The system of claim 1, wherein the dispenser is an electrical device.

13. The system of claim 1, wherein the cartridge has at least one opening from which the product is dispensed to the user upon, the cartridge having an internal conduit between the reservoir and the at least one opening, the conduit separate from the control base.

14. A multi-modal product dosing system with cross-modality tracking and lockout, characterized by a control base having a housing at least partially enclosing a cartridge receiver, a cartridge reader, at least one lockout deactivator, a wireless transceiver and a controller structured and arranged to operate the cartridge reader, the at least one lockout deactivator and the wireless transceiver to communicate information with at least one remote computing device, the control base structured and arranged to couple to one of a plurality of different cartridges, each cartridge remaining at least partially external to the housing of the control base and at least two cartridges having different modalities of delivery for a product contained therein, each of the plurality of cartridges characterized by:
a housing at least partially enclosing:
a reservoir of product;
a dispenser structured and arranged to dispense a predetermined amount of product by a predetermined modality of delivery, at least a portion of the dispenser external to the housing of the control base;
at least one data chip structured and arranged to store data regarding the cartridge;
a unique identifier associated with the cartridge and the product, the unique identifier structured and arranged to be determined by the control base;
at least one electrical contact to receive power from the control base for activation of the dispenser; and
at least one lockout mechanism structured and arranged to lockout the dispenser to prevent dispensation of the product even when the cartridge is coupled to the control base, unless the lockout mechanism of the cartridge is disengaged by the lockout deactivator of the control base, and wherein activation of any cartridge following a completed administration of product is inhibited unless authorized.

15. The system of claim 14, wherein one of the plurality of different cartridges is selected from a group consisting of: an inhalation cartridge, a topical spray cartridge, a topical liquid dropper, a strip delivery cartridge, a topical gel cartridge, a tablet cartridge, and an injection cartridge.

16. The system of claim 14, wherein the dispenser of one of the plurality of different cartridges further includes a cycloidal gear assembly to actuate a plunger against the reservoir of product to extrude a metered dose of product.

17. The system of claim 14, wherein a first lockout mechanism of the at least one lockout mechanism is structured and arranged as a cartridge lockout and a second lockout mechanism of the at least one lockout mechanism is structured and arranged as a dose lockout.

18. The system of claim 14, wherein at least one of the plurality of different cartridges further includes a vaporizing chamber structured and arranged to receive a metered dose of product from the reservoir, the reservoir thermally isolated from the vaporizing chamber.

19. The system of claim 14, wherein at least one of the at least one remote computing devices provides a database, the database further comprising:
user data for each user known to the database;
control base data for each of the control bases as related to at least one user known to the database;
product data correlated to one or more unique identifiers known to the database, the at least one unique identifiers further correlated to one or more of the plurality of different cartridges;
the database permitting correlation of the user data to the control base data and the product data to permit tracking of each product by each user and the product provided by each cartridge;

wherein the database further provides at least one operation to add a new user and/or product data to the database.

20. The system of claim 19, wherein the database further provides operational settings for control of the dispenser in response to the unique identifier associated with the engaged cartridge identified by the control base.

21. The system of claim 19, wherein the database further provides authorization for use of the cartridge in accordance with at least one element selected from the group consisting of: the user's location, the user being authorized to receive the dose, the user requesting the dose at an approved time, the user requesting the dose within an approved time window, the user being an authorized user of the dosing device, the user being a registered owner of the cartridge.

22. The system of claim 19, wherein authorization for the control base lockout deactivator to disengage the lockout device of the cartridge temporarily coupled thereto is based at least in part on wireless communication with the database to determine whether a dose has been administered from any cartridge, and to automatically inhibit activation of any other cartridge until a subsequent authorization is received.

23. The system of claim 14, wherein the cartridge has at least one opening from which the product is dispensed to the user upon, the cartridge having an internal conduit between the reservoir and the at least one opening, the conduit separate from the control base.

24. A multi-modal product dosing system with cross-modality tracking and lockout, characterized by a control base having a housing at least partially enclosing a cartridge receiver, a cartridge reader, at least one lockout deactivator, a wireless transceiver and a controller structured and arranged to operate the cartridge reader, the at least one lockout deactivator and the wireless transceiver to communicate information with at least one remote computing device, the control base structured and arranged to couple to one of a plurality of different cartridges, each cartridge remaining at least partially external to the housing of the control base and at least two cartridges having different modalities of delivery for a product contained therein, each of the plurality of cartridges characterized by:

a housing at least partially enclosing:
 a reservoir of product;
 a dispenser structured and arranged to dispense a predetermined amount of product by a predetermined modality of delivery, at least a portion of the dispenser external to the housing of the control base;
 at least one opening from which the product is dispensed to the user, the cartridge having an internal conduit between the reservoir and the at least one opening, the conduit separate from the control base;
 at least one data chip structured and arranged to store data regarding the cartridge;
 a unique identifier associated with the cartridge and the product, the unique identifier structured and arranged to be determined by the control base;
 at least one electrical contact to receive power from the control base for activation of the dispenser; and
 at least one lockout mechanism structured and arranged to lockout the dispenser to prevent dispensation of the product even when the cartridge is coupled to the control base, unless the lockout mechanism of the cartridge is disengaged by the lockout deactivator of the control base, and wherein activation of any cartridge following a completed administration of product is inhibited unless authorized.

25. The system of claim 24, wherein one of the plurality of different cartridges is selected from a group consisting of: an inhalation cartridge, a topical spray cartridge, a topical liquid dropper, a strip delivery cartridge, a topical gel cartridge, a tablet cartridge, and an injection cartridge.

26. The system of claim 24, wherein the dispenser of one of the plurality of different cartridges further includes a cycloidal gear assembly to actuate a plunger against the reservoir of product to extrude a metered dose of product.

27. The system of claim 24, wherein a first lockout mechanism of the at least one lockout mechanism is structured and arranged as a cartridge lockout and a second lockout mechanism of the at least one lockout mechanism is structured and arranged as a dose lockout.

28. The system of claim 24, wherein at least one of the plurality of different cartridges further includes a vaporizing chamber structured and arranged to receive a metered dose of product from the reservoir, the reservoir thermally isolated from the vaporizing chamber.

29. The system of claim 28, wherein the database further provides operational settings for control of the dispenser in response to the unique identifier associated with the engaged cartridge identified by the control base.

30. The system of claim 28, wherein the database further provides authorization for use of the cartridge in accordance with at least one element selected from the group consisting of: the user's location, the user being authorized to receive the dose, the user requesting the dose at an approved time, the user requesting the dose within an approved time window, the user being an authorized user of the dosing device, the user being a registered owner of the cartridge.

31. The system of claim 28, wherein authorization for the control base lockout deactivator to disengage the lockout device of the cartridge temporarily coupled thereto is based at least in part on wireless communication with the database to determine whether a dose has been administered from any cartridge, and to automatically inhibit activation of any other cartridge until a subsequent authorization is received.

32. The system of claim 24, wherein at least one of the at least one remote computing devices provides a database, the database further comprising:
 user data for each user known to the database;
 control base data for each of the control bases as related to at least one user known to the database;
 product data correlated to one or more unique identifiers known to the database, the at least one unique identifiers further correlated to one or more of the plurality of different cartridges;
 the database permitting correlation of the user data to the control base data and the product data to permit tracking of each product by each user and the product provided by each cartridge;
 wherein the database further provides at least one operation to add a new user and/or product data to the database.

* * * * *